United States Patent
Ganesh et al.

(10) Patent No.: US 12,167,907 B2
(45) Date of Patent: Dec. 17, 2024

(54) WIRELESS SYSTEM AND METHODS FOR REMOTE ISCHEMIC CONDITIONING, EXTERNAL COUNTERPULSATION, OTHER CUFF-BASED THERAPIES, AND PATIENT MONITORING

(71) Applicants: Aravind Ganesh, Calgary (CA); Ryan Rosentreter, Calgary (CA); Maliyat Noor, Calgary (CA); Noam Anglo, San Jose, CA (US); Kyle Guild, Calgary (CA)

(72) Inventors: Aravind Ganesh, Calgary (CA); Ryan Rosentreter, Calgary (CA); Maliyat Noor, Calgary (CA); Noam Anglo, San Jose, CA (US); Kyle Guild, Calgary (CA)

(73) Assignee: SNAP DX INC. (CA)

( * ) Notice: Subject to any disclaimer, the term of this patent is extended or adjusted under 35 U.S.C. 154(b) by 93 days.

(21) Appl. No.: 17/317,771

(22) Filed: May 11, 2021

(65) Prior Publication Data
US 2021/0353157 A1 Nov. 18, 2021

Related U.S. Application Data

(60) Provisional application No. 63/024,239, filed on May 13, 2020.

(51) Int. Cl.
*A61B 5/0205* (2006.01)
*A61B 5/00* (2006.01)

(52) U.S. Cl.
CPC .......... *A61B 5/0205* (2013.01); *A61B 5/0004* (2013.01); *A61B 5/0024* (2013.01); *A61B 5/4836* (2013.01); *A61B 5/6823* (2013.01); *A61B 2562/0219* (2013.01)

(58) Field of Classification Search
None
See application file for complete search history.

(56) References Cited

U.S. PATENT DOCUMENTS

| | | | | |
|---|---|---|---|---|
| 2010/0105993 A1* | 4/2010 | Naghavi | ............ | A61B 17/1355 600/301 |
| 2010/0324429 A1* | 12/2010 | Leschinsky | ........ | A61B 5/02233 600/499 |
| 2012/0265240 A1* | 10/2012 | Ganske | ............ | A61B 17/1355 606/202 |
| 2013/0172691 A1* | 7/2013 | Tran | ........ | A61B 8/565 600/595 |
| 2014/0094677 A1* | 4/2014 | Okuda | ................ | A61B 5/6823 600/390 |
| 2014/0276123 A1* | 9/2014 | Yang | ...................... | G16H 40/63 600/513 |
| 2019/0184206 A1* | 6/2019 | Nazer | ...................... | A61N 7/02 |

* cited by examiner

*Primary Examiner* — Devin B Henson
*Assistant Examiner* — Matthew Eric Ogles
(74) *Attorney, Agent, or Firm* — Kirsten M. Oates; Rodman & Rodman LLP

(57) ABSTRACT

Wireless systems and methods are provided for protecting vital organs from blood flow loss, and for physiological monitoring of a subject in various settings. The systems and methods permit the coordinated delivery of various treatment protocols involving inflation or deflation of cuffs to multiple limbs of the subject.

22 Claims, 16 Drawing Sheets

WIRELESS SYSTEM AND METHODS FOR REMOTE ISCHEMIC CONDITIONING, EXTERNAL COUNTERPULSATION, OTHER CUFF-BASED THERAPIES, AND PATIENT MONITORING

FIELD OF THE INVENTION

The present invention relates to wireless systems and methods for protecting vital organs from blood flow loss, and for physiological monitoring of a subject in various settings. In particular, the systems and methods permit the coordinated delivery of various treatment protocols involving inflation or deflation of cuffs to multiple limbs of the subject.

BACKGROUND OF THE INVENTION

Ischemic diseases like stroke, cerebral small-vessel disease, and myocardial infarction are caused by a loss of blood flow to a critical organ. Restoration of blood flow requires emergent treatment which is preferably performed at a treatment facility; however, unavoidable transport delay which typically occurs from the onset location to the treatment facility makes many patients ineligible for treatment upon arrival. There is thus an urgent need for treatments that can be safely administered remotely; for example, at the onset location or in an ambulance.

Experimentally inducing brief periods of ischemia-reperfusion that do not result in tissue injury before or during an ischemic event can reduce subsequent injury. This process is known as ischemic conditioning which can be subdivided into pre-conditioning (if before the event) or per-conditioning (during the event but before restoration of blood flow or reperfusion), or post-conditioning (after the event and during or after reperfusion).[1] Ischemic conditioning is thought to induce an endogenous protective environment, consisting of humoral and neuronal-mediated responses that promote cell survival and repair and inhibit or dampen apoptotic and inflammatory pathways, helping mitigate ischemic injury.[2] These protective mechanisms do not appear to be organ-specific, exerting systemic and remote protective effects; thus, remote ischemic pre-conditioning ("RIC") applied to a limb can promote tolerance to cerebral ischemia.[1] The RIC stimulus appears to precipitate not only an early phase of short-term metabolic, energy utilization, and blood-flow changes lasting a few hours, but also a late phase consisting of longer-lasting changes in gene expression, inflammatory, and oxidative pathways (16-96 hours post-RIC).[3]

Though the exact mechanisms for signal transmission from the periphery to the brain to protect against ischaemia remain unclear, putative pathways include humoral mechanisms involving nitric oxide, nitrite, microRNA-144, and SDF-1-alpha; immune and/or anti-inflammatory pathways; and neuronal mechanisms involving activation of peripheral sensory fibers.[4] Consequently, there is also uncertainty regarding the optimal biomarkers for RIC, with candidate biomarkers including circulating nitrite, heat shock protein 27 (HSP-27), microRNA-144, and interleukin-10.[5-7]

Various prior art devices and systems for delivering RIC treatment protocols involve cuff inflation and deflation. The most commonly used protocol with arm cuffs consists of inflation to 200 mmHg for 5-minutes followed by 5-minutes deflation typically for four or five cycles in a single treatment sitting.[8] Some of these systems measure blood pressure (BP) to tailor treatment to the patient's BP (e.g. inflating up to 20 mmHg above systolic pressure) and can store details within the device about treatments performed and BPs measured.

Two recent systematic reviews of RIC for percutaneous coronary intervention (PCI) in the setting of acute myocardial infarction (AMI)[9, 10] or elective PCI[10] find higher myocardial salvage and lower infarct volumes compared to controls, with fewer major adverse cardiovascular events. In contrast, a meta-analysis of RIC prior to cardiac surgery found no benefits for post-operative myocardial infarction or mortality.[11] A negative interaction between RIC and propofol anesthesia was hypothesized to underlie the lack of effect in cardiac surgery,[11] and may explain the discrepant findings in PCI trials compared to cardiac surgery trials. Human trials of remote ischemic pre-conditioning have also been undertaken in the past few years in the field of cerebrovascular disease, mostly applied to the upper-limb but some in the lower-limb,[12-17] as have a couple of studies of peri-/post-conditioning (happening after ischemic/hemorrhagic injury) .[8, 18, 19] Bilateral upper-limb RIC, using an automated device specifically developed for this purpose, has been shown to protect against recurrent stroke in intracranial arterial stenosis.[13]

There is preliminary evidence of efficacy for this therapy in cerebral small vessel disease. A trial of 17 patients with cSVD randomized to RIC or sham-RIC reported improved mean flow velocity of the middle cerebral artery, lower dizziness handicap inventory score, and lower post-treatment white matter hyperintensity (WMH) volume in the RIC group.[14] A trial in 36 patients with cSVD reported a significant reduction in WMH volume at 1 year compared to sham-RIC and a significant difference on visuospatial and executive function sections of the Montreal Cognitive Assessment (MoCA), though there was no significant change in the number of lacunes.[15] The RIC group also attained lower plasma triglyceride, total cholesterol, low density lipoprotein, homocysteine levels, and middle cerebral artery pulsatility indices. These studies have been small and essentially hypothesis-generating. It remains unclear what doses of chronic daily RIC are tolerable and safe, whether RIC effects persist after cessation of treatment, and what biomarkers are optimal for treatment response.

Thousands of patients have undergone RIC, including severely ill patients like those undergoing major vascular surgery, and no major adverse events have been reported. However, proposed contraindications include any vascular, soft-tissue, or orthopedic injury that contraindicates arm ischemic preconditioning or history of peripheral vascular disease, such as subclavian or other upper limb arterial stenosis or occlusion. Patients on anticoagulants have often been excluded given the risk of cuff pressure-related bruising or bleeding.

Most existing systems use wires going from a hub to the limb cuff to deliver therapy. They are typically intended only for single-limb therapy, but a few that are capable of two-limb therapy require wires running from each cuff to the same hub that controls inflation/deflation. The presence of wires going from a hub to the limbs makes RIC a cumbersome therapy to deliver. A relatively more compact system has been described by CellAegis Inc. that delivers RIC therapy to a single limb with the inflation/deflation hub directly attached to a detachable limb cuff. However, it is important to be able to vary the intensity of therapy from one limb to multiple limbs to test dose-response relationships effectively in clinical trials of RIC.

Furthermore, there is a need for these systems to be capable of also being programmed to deliver other types of cuff-based protocols, should the repetitive inflation/deflation cycles of RIC not prove to be the most beneficial approach for a given scenario, like preventing further damage in an ongoing acute ischemic stroke versus the prevention of future stroke. An alternative protocol may include having blood pressure cuffs persistently inflated to a sub-ischemic threshold to encourage redirection of blood to the brain, potentially mimicking the effect of the invasive CoAxia abdominal aortic partial occlusion device, which showed promising results in the SENTIS trial.[20, 21] Another example is external counterpulsation ("ECP") therapy. As used herein, the term "ECP" therapy refers to a strategy by which the perfusion to vital organs is enhanced. This is achieved via increased blood pressure during heart diastole and reduced blood pressure during heart systole. The most common non-invasive method for this blood pressure modulation is enacted by pneumatic cuffs around the lower limbs which are deflated to a pressure below systolic blood pressure at the onset of systole and inflated to a pressure above the systolic blood pressure during diastole. The signal for systole and diastole is obtained by measuring electrical activity of the heart via electrocardiography or ECG.[22] ECP permits blood to be pumped more easily from the heart, and may encourage blood vessels to open small channels that become extra branches, known as channels or collaterals, that can potentially act as "natural bypass" vessels to provide improved blood flow to vital structures like the heart and brain. ECP has been shown to be effective in improving outcomes for patients with cardiovascular conditions[23] and has been shown to be both safe and feasible in patients within 48 hours of ischemic stroke[24] while potentially improving neurological outcomes during stroke recovery.[25, 26] The use of ECP therapy in the acute stroke setting or as a home-based therapy for prevention of stroke or vascular dementia has not been evaluated to date. This is partly due to the limitations of current ECP therapy devices currently available which are cumbersome, often with a full-sized bed and monitor[27-29] that makes them ineligible for the pre-hospital, emergency, or surgical setting. These limitations, in addition to the requirement of a trained operator, also make conventional options for ECP therapy impractical for patient use in their own home.

Current devices that can deliver RIC or ECP generally are not able to deliver alternative cuff-based treatment protocols and do not have monitoring capabilities beyond simple blood pressure measurement. Information may be stored on some of these devices but real-time data visualization of trends and other parameters is not available. RIC or ECP systems have to be able to fulfil relevant clinical needs (like monitoring) beyond the therapy itself, without getting in the way of the clinical team, in order to gain traction for use in high-stakes settings like ambulances and operation theatres that are already crowded by various devices and appliances attached to the patient.

SUMMARY OF THE INVENTION

The present invention relates to wireless systems and methods for protecting vital organs from blood flow loss, and for physiological monitoring of a subject in various settings. In particular, the systems and methods permit the coordinated delivery of various treatment protocols involving inflation or deflation of cuffs to multiple limbs of the subject. It was discovered that by using the systems and methods of the present invention one or more of the following benefits may be realized, as will be herein described:

A wireless system for multi-limbed delivery of RIC, ECP, and other cuff-based therapies.

Multiple treatment protocols may be administered.

The different treatment protocols can be programmed through the central hub by a user at the hub, via standalone cuff modules, or remotely by an off-site clinician.

Incorporation of wireless physiological monitoring of multiple parameters that are stored, wirelessly transmitted, and analyzed.

A built-in monitoring method to quantify clinically relevant stroke progression.

A central hub that provides near-real-time data visualization and allows for data entry, remote transmission and data visualization.

Anonymized data aggregation and analysis; and

Added safety features.

Broadly, in one aspect, the invention comprises a system for preventing, treating, or alleviating ischemic disease in a subject comprising: a central hub, and a plurality of cuff modules in wireless communication with the central hub, the cuff modules being connectable and mountable to corresponding limb cuffs positioned on the subject, wherein the central hub activates the cuff modules to inflate or deflate the limb cuffs. In the various embodiments, the limb cuffs comprise blood pressure cuffs. In the various embodiments, the system further comprises additional cuffs around one or more of subject's hips, buttocks, and abdomen.

In the various embodiments, the cuff module is configured to monitor a first set of parameters selected from systolic and diastolic blood pressure, heart rate, oxygen saturation, accelerometry, and photoplethysmography.

In the various embodiments, the system further comprises one or more sensors attachable to body parts other than limbs for monitoring a second set of parameters. In the various embodiments, the one or more sensors are selected from an electrocardiogram module, a pulse oximeter, an electroencephalography module, a near infrared spectroscopy, a light-emitting diode, or an electrode-based sensor. In the various embodiments, the sensors are communicatively coupled to the central hub through wireless connection or through wired connection with the cuff modules.

In the various embodiments, the cuff module comprises a housing having a front portion, a back portion, side portions, a top portion, a bottom portion, and defining an inner cavity for encasing one or more components. In the various embodiments, the bottom portion defines an aperture configured for receiving and accommodating a power switch to activate or deactivate the cuff module, one or more input/outputs for connecting the sensors, and a charging port. In the various embodiments, the bottom portion defines a cuff air outlet for receiving an air line, the air line connecting the cuff module to the limb cuff and allowing passage of air therethrough to inflate or deflate the limb cuff. In the various embodiments, the system further comprises mounting members for attaching the cuff module to the limb cuff. In the various embodiments, the top and bottom portions define aligned outwardly extending protrusions configured for receiving corresponding mounting members, the mounting members comprising posts oriented parallel to each other and offset from the side portions to define slots therebetween for threading the limb cuff.

In the various embodiments, the components comprise one or more of a battery, a microcontroller, an air pump, a pressure sensor, a solenoid valve, an accelerometer, a speaker, a buzzer, and an additional control button for stand-alone operation. In the various embodiments, the microcontroller comprises a wireless transceiver for receiving commands from the central hub and for transmitting signals representing data received from the components to the central hub. In the various embodiments, the central hub receives, collects, and stores data on one or more cloud-based servers for display on one or more dashboard user interfaces configured to allow a user to download the data using a smartphone, tablet, or personal computer. In the various embodiments, the air pump and the solenoid valve cooperate to inflate and deflate the limb cuffs.

In another aspect, the invention comprises a method for preventing, treating, or alleviating ischemic disease in a subject using the above system, comprising positioning the limb cuffs and corresponding cuff modules on the subject's limbs; and activating the system to inflate or deflate the limb cuffs and to monitor one or more parameters representative of the subject's physiological condition in accordance with a selected treatment protocol. In the various embodiments, the treatment protocol comprises remote ischemic conditioning therapy with different thresholds or durations of inflation and deflation, external counterpulsation therapy, or sustained inflation to sub-systolic pressures.

In the various embodiments, the method further comprises positioning additional cuffs around the subject's hips, buttocks, or abdomen. In the various embodiments, the method further comprises positioning sensors on the subject's body. In the various embodiments, the treatment protocol comprises remote ischemic conditioning therapy with different thresholds or durations of inflation and deflation, external counterpulsation therapy, or sustained inflation to sub-systolic pressures.

Additional aspects and advantages of the present invention will be apparent in view of the description, which follows. It should be understood, however, that the detailed description and the specific examples, while indicating preferred embodiments of the invention, are given by way of illustration only, since various changes and modifications within the scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings.

DETAILED DESCRIPTION OF PREFERRED EMBODIMENTS

Figure 1:
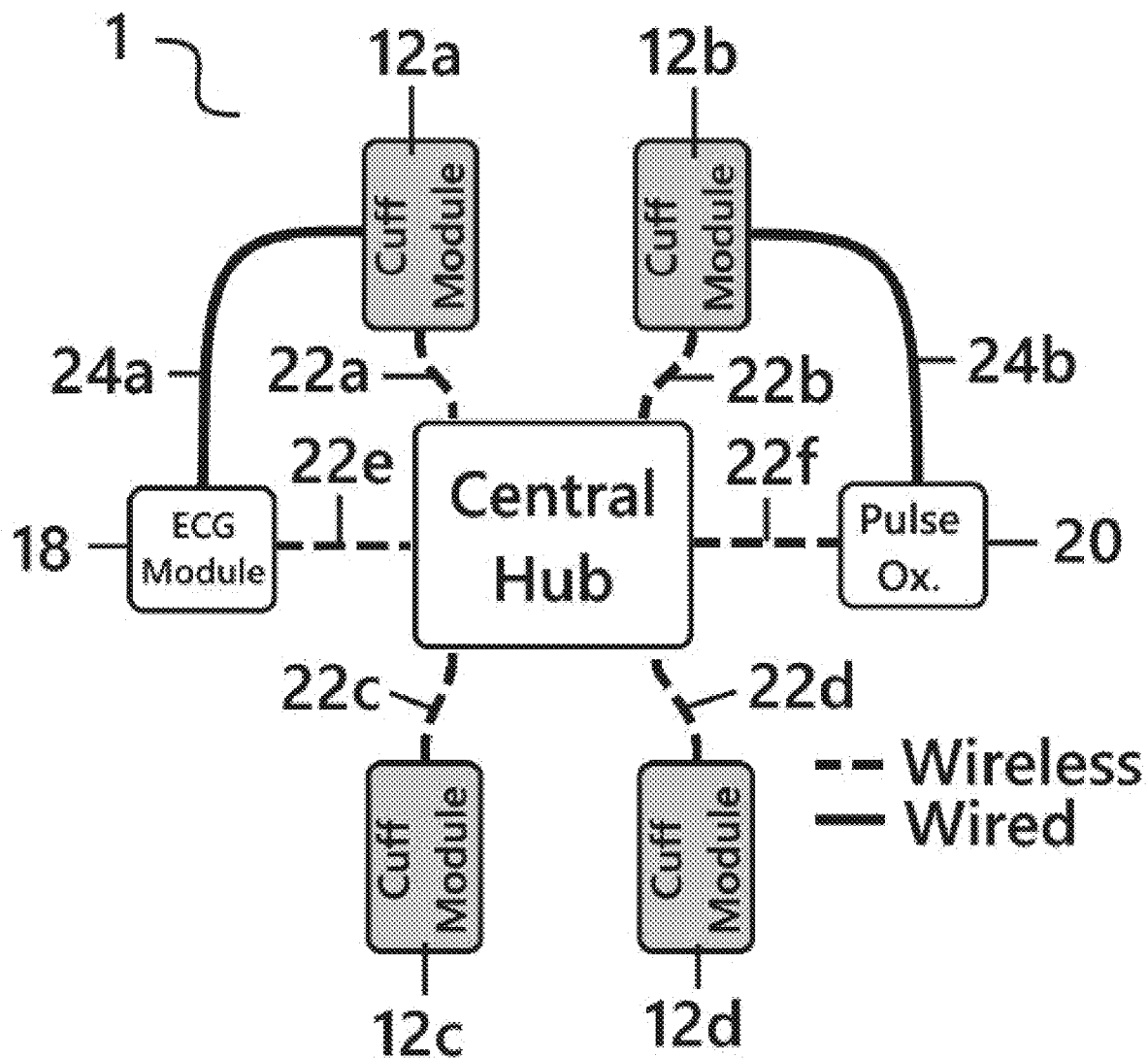
FIG. 1 is a schematic view of a first embodiment of a system of the invention.

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a," "an," and "the" include plural referents unless the context clearly dictates otherwise.

The present invention relates to systems and methods for protecting critical organs from a loss of blood flow due to a disease condition, and for physiological monitoring of a subject in various case scenarios. As used herein, the term "critical organ" refers to an organ including, but not limited to, the brain and heart. As used herein, the term "disease condition" refers to any disorder which results in a loss of blood flow. In the various embodiments, the disease condition is ischemic disease which includes, but is not limited to, stroke, cerebral small-vessel disease, myocardial infarction, and the like. As used herein, the term "subject" refers to any member of the animal kingdom. In one embodiment, a subject is a child or adult human patient.

In the various embodiments, the invention comprises systems and method which permit the coordinated delivery of various treatment protocols involving inflation or deflation of cuffs to multiple limbs of the subject. The system also incorporates measurement and monitoring of various physiological and limb-specific parameters, with secure storage, analysis, and remote transmission of treatment and monitoring data to a cloud-based server. The system allows input of treatment parameters, visualization of treatment and monitoring data, and entry of clinical data. The system also relays warnings based on monitoring data and can auto-terminate treatment protocols in the interest of patient safety.

In the various embodiments, the system can deliver coordinated remote ischemic conditioning ("RIC") therapy, external counterpulsation ("ECP") therapy, and other cuff-based therapies through limb-attached devices for up to four limbs. As used herein, the term "RIC" therapy refers to a tissue-protective strategy of cyclical cuff inflation and deflation, each of several minutes duration which may promote cell survival and repair, while inhibiting cellular death and inflammatory pathways. As used herein, the term "ECP" therapy refers to a strategy by which the perfusion to vital organs is enhanced via increasing blood pressure during heart diastole and reduced blood pressure during heart systole. The system is modular so the intensity of therapy can easily be varied from one limb to multiple limbs to test dose-response relationships, and system can also be programmed to deliver any other cuff-based protocol, such as sustained inflation to a sub-systolic pressure. The system incorporates multi-modal physiological monitoring through additional built-in or interconnected sensors, provides users with near-real-time dynamic data visualizations of any monitored parameter of interest as well as treatment details, and transmits and analyzes this data remotely. The system is wireless, compact, and designed to minimize any disruption of routine clinical care and facilitate routine aspects of patient assessment and monitoring beyond the delivery of RIC, ECP, or other cuff-based therapies.

Figure 2:
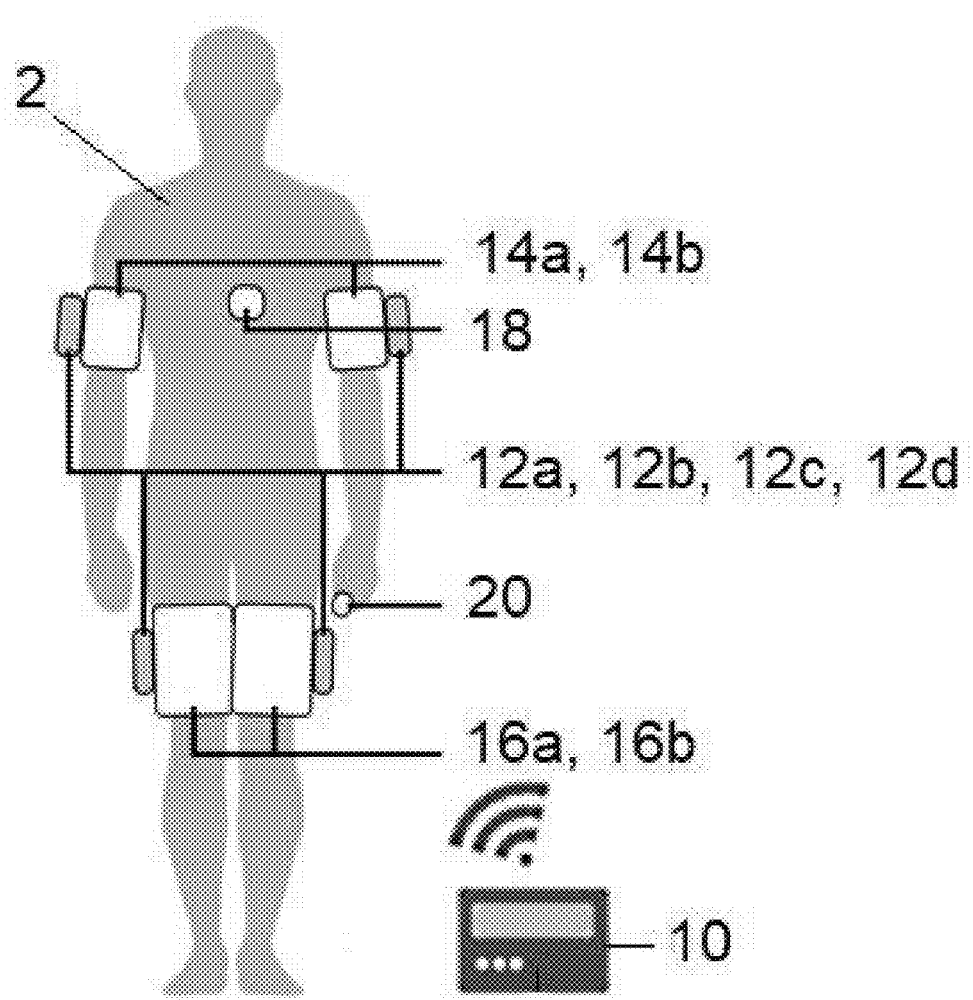
FIG. 2 is a schematic view of the system of FIG. 1 in use on a subject's body.

Referring to FIGS. 1-2, an exemplary system (1) of the invention includes at least a central hub (10) and a plurality of cuff modules (12a, 12b, 12c, 12d) in wireless communication (22a, 22b, 22c, 22d, 22e, 22f) with the central hub (10) and which are connectable and mountable to corresponding arm cuffs (14a, 14b) and leg cuffs (16a, 16b) positioned on the subject's limbs. In the various embodiments, the arm cuffs (14a, 14b) and leg cuffs (16a, 16b) may be blood pressure cuffs. In this manner, the system (1) enables simultaneous or sole monitoring of parameters of interest in the different limbs including, but not limited to, systolic and diastolic blood pressure, heart rate, oxygen saturation, accelerometry, and photoplethysmography (i.e., blood volume changes in the vessels).

In the various embodiments, the system (1) may include one or more peripheral devices including, but not limited to, sensors which are attached to parts of the body other than the limbs to integrate physiological monitoring of additional parameters including, but not limited to, heart rhythm, oxygen saturation of the blood, cerebral blood flow, electrical brain activity, and the like. Non-limiting examples of sensors include an electrocardiogram ("ECG") module (18), a pulse oximeter (20), an electroencephalography module, near infrared spectroscopy, and the like.

In the various embodiments, the central hub (10) communicates with the cuff modules (12a, 12b, 12c, 12d) and sensors (18, 20). In the various embodiments, the central hub (10) may transmit signals to, and may also receive and be responsive to signals from the cuff modules (12a, 12b, 12c, 12d) and the sensors (18, 20). In this manner, multiple parameters may be collected, recorded, stored, wirelessly transmitted, and analyzed. The data may be analyzed in the context of the subject's demographics and a log maintained of the readings. Besides showing the recorded readings, the system (1) maintains an updated log including, but not limited to, auto-calculated mean arterial pressure, mean systolic/diastolic blood pressure, minimal and maximal recorded systolic/diastolic pressure, blood pressure variability, and heart rate variability.

In the various embodiments, the central hub (10) provides near-real-time data visualization and permits data entry. The central hub screen displays not only relevant physiological readings from the last measurement but also provides a graphical visualization of the trends in the data since the monitoring or treatment began (with a modifiable time window). The display can be customized to show any collected metric of interest for the viewer. Granular treatment details can also be visualized with a couple of button clicks, showing cycle parameters and settings, specific timing of occlusion and reperfusion cycles, and holding-pressure settings. Data entry is also permitted through the central hub (10) for key patient characteristics, examination findings, treatment, etc.

Figure 6:
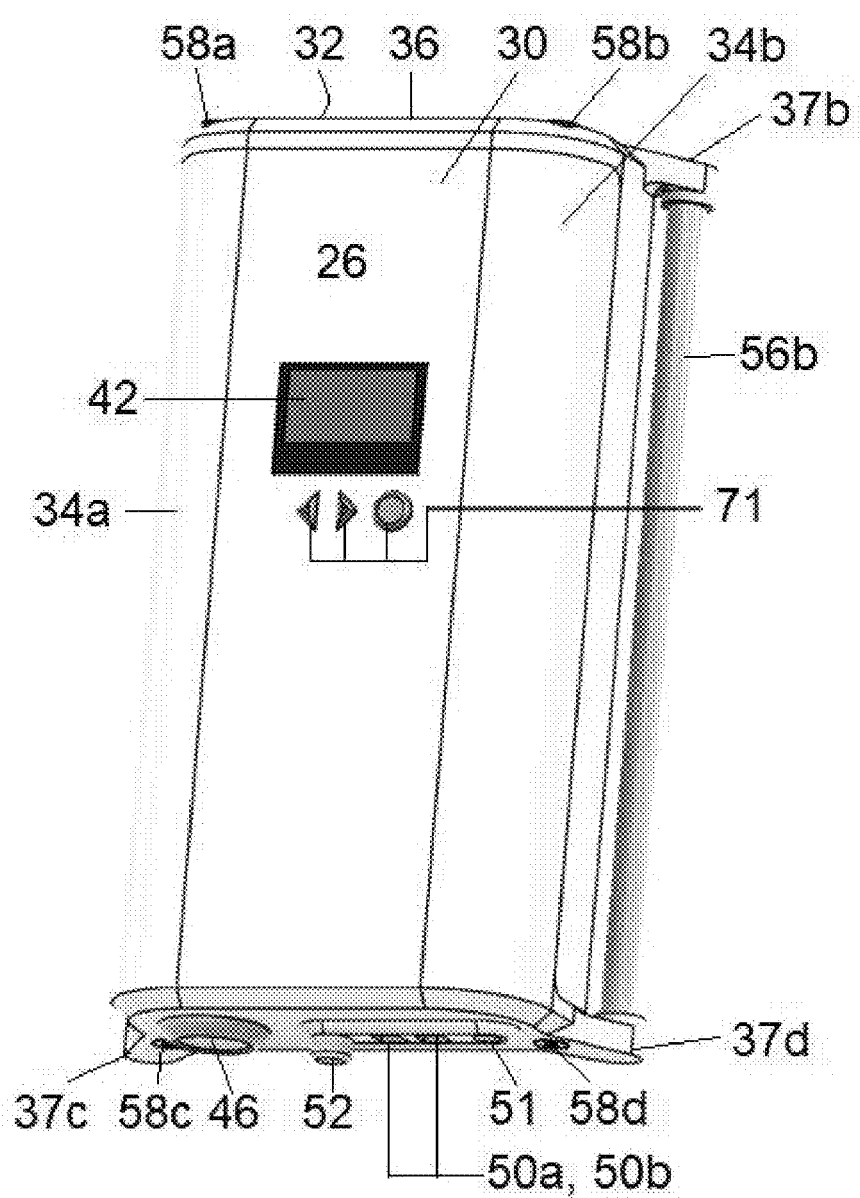
FIG. 6 is a perspective view of a second embodiment of a cuff module for use with the system of FIG. 1 including one or more additional control buttons for stand-alone activation, deactivation, and programming of remote ischemic conditioning or other cuff-based therapies.

In the various embodiments wherein the system (1) does not include a central hub (10) or wireless communication (22a, 22b, 22c, 22d, 22e, 22f), or in the event of failure or unavailability of the central hub (10) or wireless communication (22a, 22b, 22c, 22d, 22e, 22f) for whatever reason, each cuff module (12a, 12b, 12c, 12d) is also configured to operate as a standalone device for RIC or ECP therapy. For such purpose, each cuff module (12a, 12b, 12c, 12d) includes one or more additional control buttons (71) that provide the same activation or deactivation, cuff-based therapy protocol programming, and data displaying functionality that would otherwise be provided by the central hub (10) (FIG. 6). The buttons (71) may comprise, for example, left and right control arrows, push control buttons, and the like.

In the various embodiments, the central hub (10) may include provisions to store and secure up to four cuff modules (12a, 12b, 12c, 12d), with or without a blood pressure cuff (14a, 14b, 18a, 18b). This storage mechanism could also act as a charging dock for the cuff modules (12a, 12b, 12c, 12d). In the various embodiments wherein the system (1) does not include a central hub (10), a storage or charging dock that holds only a single cuff module may instead be utilized.

In the various embodiments, an internal speaker or buzzer (not shown) is included as part of the internal electronics of the central hub (10) or cuff modules (12a, 12b, 12c, 12d) for the purpose of adding auditory feedback as therapy progresses from one cycle to the next. In such a configuration, the speaker may beep as an inflation starts, and beep again as a deflation starts. Within the software, a "silent mode" is included to disable the speaker in certain scenarios that require fewer noise or distractions. Such scenarios would include situations where the system is used to prevent ischemic events like stroke during a surgery or other interventional procedure in an operating room or angiography suite. The speaker may also be enabled selectively, for example, to allow beeps in critical scenarios such as a malfunction or a safety concern identified by the device (as described below), but not in normal phase to phase transitions as part of the programmed treatment or monitoring protocol.

In the various embodiments, alongside options to adjust the speaker, decreasing or increasing the brightness of the display may also be included, for particularly dark or bright environments to facilitate data visualization and entry.

Figure 3:
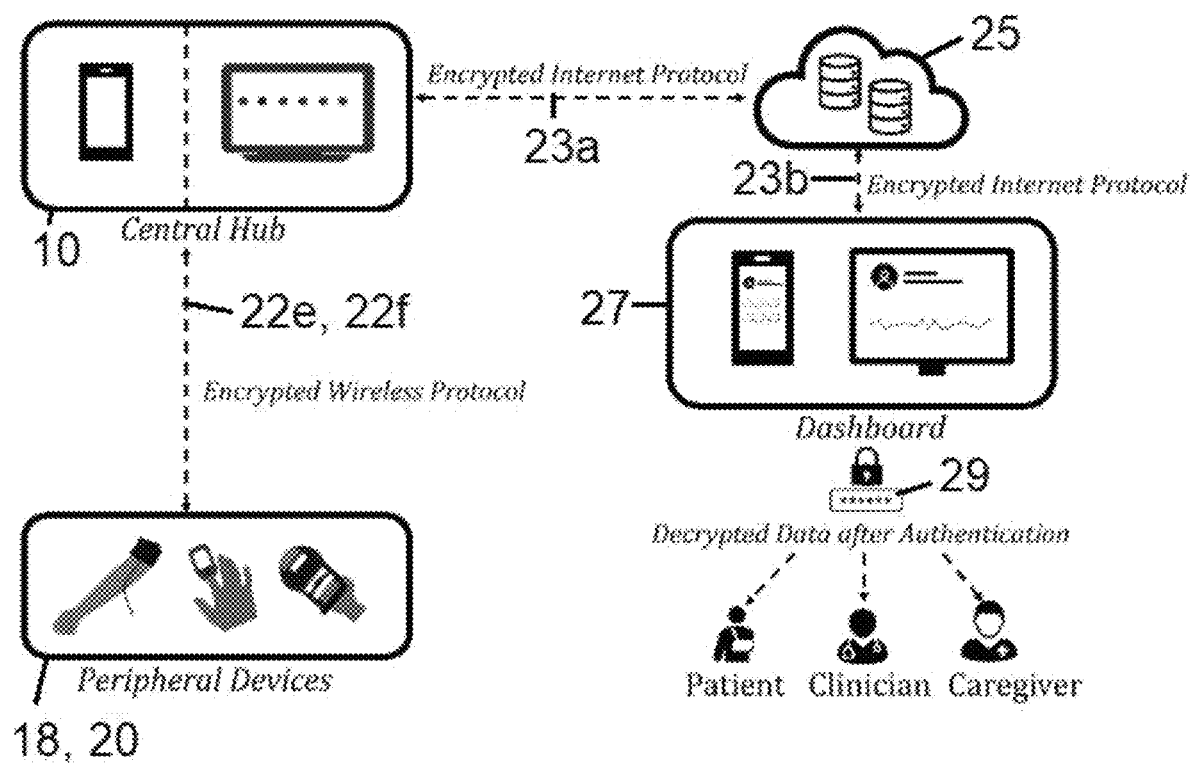
FIG. 3 is a software flow diagram of the system of FIG. 1.

In the various embodiments, the system (1) is able to remotely transmit data from the central hub (10), allowing remote data visualization (FIG. 3). The central hub (10) supports internet connections (23a, 23b) to upload data collected (for example, at home, in the ambulance, or at a remote site) to one or more cloud-based servers (25). The central hub (10) has on-board storage capabilities, whereby if there are no internet connections (23a, 23b) available, the central hub (10) will store data until internet availability resumes. A physician, other healthcare professional, or researcher at a remote site can view collected data via secure access to the cloud-based server (25). The central hub (10) can be operated also by remote transmission. Such remote operability may be beneficial in a trial setting, whereby the peripheral devices (18, 20) could be randomized centrally to deliver either a sham protocol or one of several different treatment protocols while blinding the care team and the patient.

Figure 4:
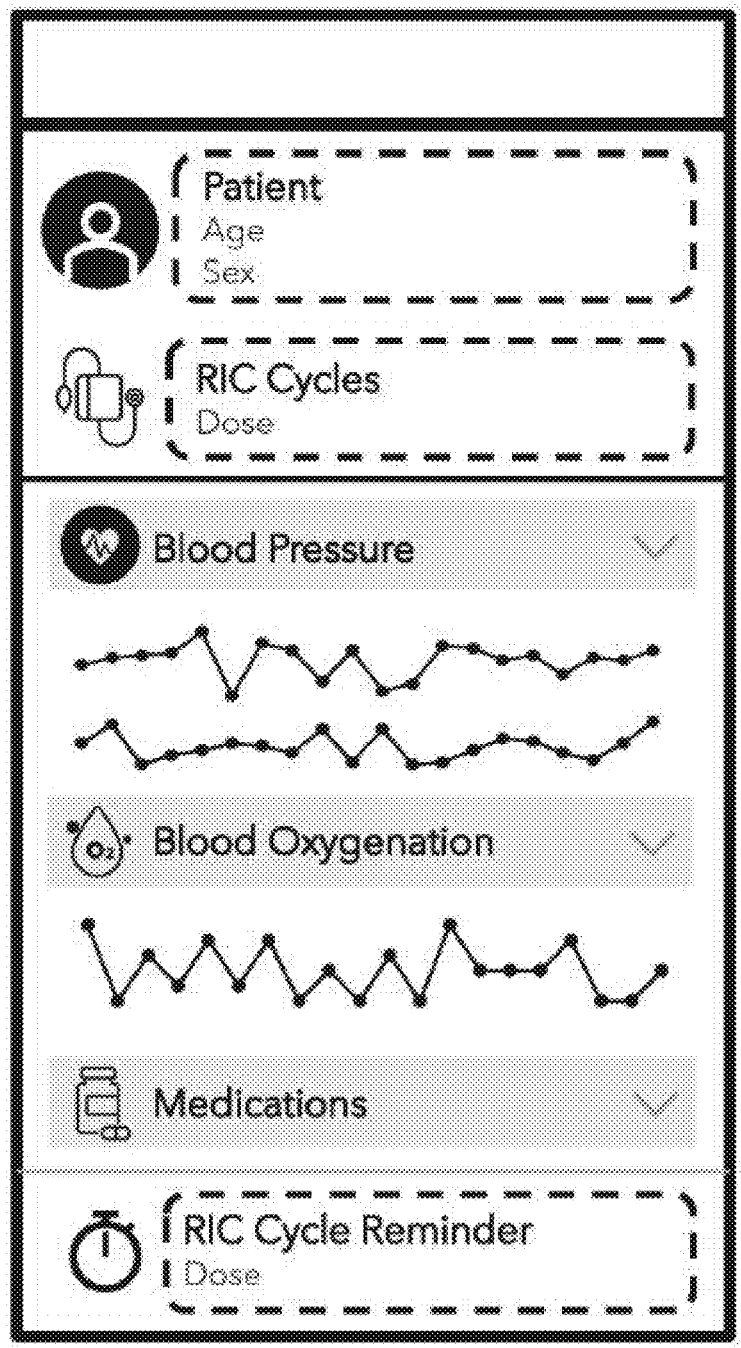
FIG. 4 is a diagram of one exemplary iteration of the dashboard user interface of FIG. 3.

In the various embodiments, the system (1) supports multiple online dashboards (27) that pull data from the cloud-based servers (25) to display patient physiological status in the ambulance, hospital, or at home to researchers or clinicians. All the data (29) shared between all wireless connections (22e, 22f, 23a, 23b) in the system are encrypted. Clinicians and researchers will be able to view and monitor a patient's status and prescribe cuff-based therapy doses remotely using the dashboards (27). The clinicians and researchers will need to provide two-factor authentication to access the patient data on the dashboards (27). The system (1) can also provide a customized patient- or caregiver-facing dashboard (FIG. 4) that contains information presented at an appropriate level for the patient, including demonstrating their monitored progress, improvement, or treatment completion record to encourage ongoing compliance and provide personalized insights.

In the various embodiments, the remotely transmitted data facilitates anonymized data aggregation and analysis. In addition to gathering and analyzing data for each individual patient to inform their care, the system (1) can also aggregate anonymized data for all patients treated/monitored with the system (1) across all devices in a central database, to allow advanced analytics with support vector machines and other machine-learning algorithms. Such algorithms can facilitate generation of predictive models to optimize RIC or other cuff-based therapy regimens for individual patients.

The cuff modules (12a, 12b, 12c, 12d) and sensors (18, 20) are communicatively coupled with the central hub (10) by respective communication lines. As used herein, the term "communicatively coupled" is intended to mean either a direct or an indirect communication connection. Such connection may be a wired or wireless connection which is well known to those skilled in the art and will therefore not be discussed in detail.

Communication to and from the central hub (10) may occur through wireless connection (22a, 22b, 22c, 22d, 22e, 22f), wired connection (24a, 24b), or a combination thereof. In the various embodiments, communication between the cuff modules (12a, 12b, 12c, 12d) and the central hub (10) preferably occurs through wireless connection (22a, 22b, 22c, 22d), with the cuff modules (12a, 12b, 12c, 12d) including their own dedicated wireless transceivers to communicate with the central hub (10). In the various embodiments, communication to and from the sensors (18, 20) and the central hub (10) may occur directly through wireless connection (22e, 22f), with the sensors (18, 20) including their own dedicated wireless transceivers to communicate with the central hub (10). In the various embodiments, communication to and from the sensors (18, 20) and the central hub (10) may occur indirectly by connecting the sensors (18, 20) to the cuff modules (12a, 12b) by wired connection (24a, 24b), and connecting the cuff modules (12a, 12b) to the central hub (10) by wireless connection (22a, 22b). In this manner, the sensors (18, 20) may utilize the wireless transceivers of the cuff modules (12a, 12b) in order to communicate with the central hub (10). In the various embodiments, wireless connection is preferable since it overcomes the problem of intrusive or cumbersome wires and allows easy, systematic testing of test dose-response to RIC, ECP, or other cuff-based therapies.

In the various embodiments, the wireless connection (22a, 22b, 22c, 22d, 22e, 22f) may comprise Bluetooth wireless technology or Adaptive Network Topology (ANT), and the like. The central hub (10) is a custom device that supports wireless connections (22a, 22b, 22c, 22d, 22e, 22f) with multiple peripheral monitoring devices, including multiple blood pressure cuffs and devices such as a pulse oximeter (18, 20). In the various embodiments, any number of input/output interfaces may be included to input or output and receive or transmit parameter and command signals. The system (1) supports wireless protocols such as Bluetooth for communication between the central hub (10) and peripheral cuffs and other sensor devices (18, 20). The central hub (10) is capable of wirelessly coordinating RIC cycles across multiple cuff configurations and collecting physiological measurements across different monitoring devices.

In the various embodiments intended for use in patient homes, the central hub (10) can be replaced by a phone-, tablet-, or other mobile device-based application designed to help the patient monitor their cuff-based therapy (like RIC or ECP) and other physiological metrics. The mobile application wirelessly connects to the multiple blood pressure cuffs and automatically coordinates treatment cycles across multiple cuffs according to the patient's prescribed treatment protocol and dose. The mobile application also uploads the patient's monitored physiological metrics to a cloud-based server (25). The application is designed to allow the patient to easily track their therapy and also monitor their recovery from conditions like stroke or heart disease by integrating data from multiple paired devices such as hand dynamometers and pedometers. The application, like the central hub (10) described above, supports wireless pairing between a mobile device and multiple blood pressure cuffs and other wireless-enabled accessories including but not limited to pulse oximeters, pedometers, etc.

In the various embodiments, the cuff modules (12a, 12b, 12c, 12d) and sensors (18, 20) all intercommunicate with the central hub (10) to perform selected functions as detailed in FIGS. 9A-11D when positioned on a subject's body (2) as shown in FIG. 2. In the various embodiments, the cuff modules (12a, 12b) may be connected to arm cuffs (14a, 14b) positioned around each of the subject's upper arms (i.e., between the shoulder and the elbow) or forearms (i.e., between the elbow and hand). In the various embodiments, the cuff modules (12c, 12d) may be connected to leg cuffs (16a, 16b) positioned around each of the subject's thighs (i.e., between the hip and the knee) or calf (i.e., between the knee and foot). It is contemplated that the number, size, positioning, and connection of cuff modules (12a, 12b, 12c, 12d), arm cuffs (14a, 14b), and leg cuffs (16a, 16b) may vary. In the various embodiments, the arm cuffs (14a, 14b)

may be commercially available or custom blood pressure cuffs. In the various embodiments, the leg cuffs (16a, 16b) may be commercially available or custom blood pressure cuffs. In the various embodiments, the cuff modules (12a, 12b, 12c, 12d) may be provided in a kit form with the arm cuffs (14a, 14b) and leg cuffs (16a, 16b) easily attachable or removable from the cuff modules (12a, 12b, 12c, 12d) for convenient repair or replacement. In situations where the system is adapted for ECP or similar cuff-based therapies, additional wide pneumatic cuffs may also be deployed that wrap around the patient's hips, buttocks, and/or abdomen.

In the various embodiments, the sensors (18, 20) may be positioned on other parts of the subject's body (2) as appropriate. In the various embodiments, the ECG module (18) is positioned on the subject's chest in the vicinity of the heart to detect heart rhythm. In the various embodiments, the pulse oximeter (20) is positioned on a fingertip of the subject to detect the oxygen saturation of the blood.

Figure 5A:
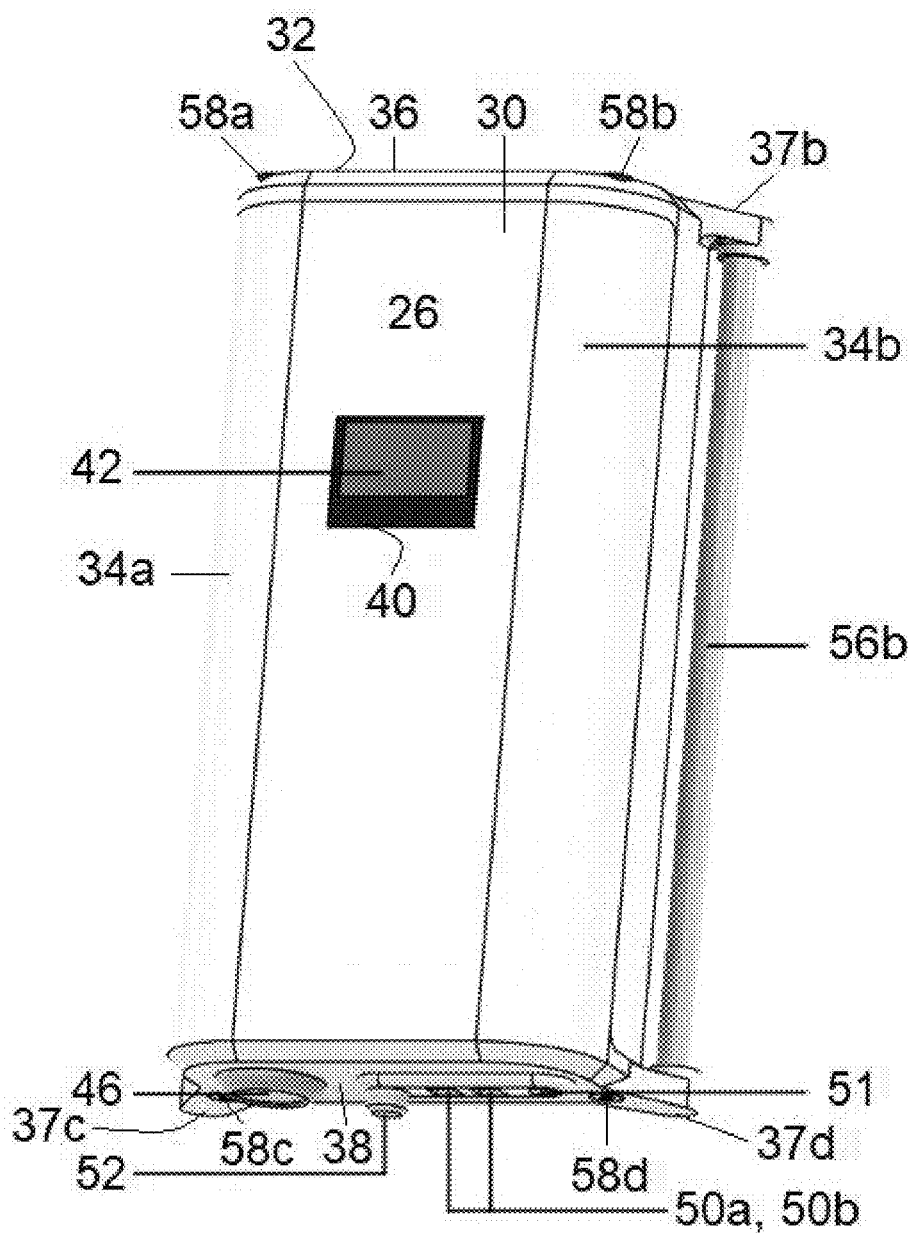
FIG. 5A is a perspective view of a first embodiment of a cuff module for use with the system of FIG. 1.
Figure 5B:
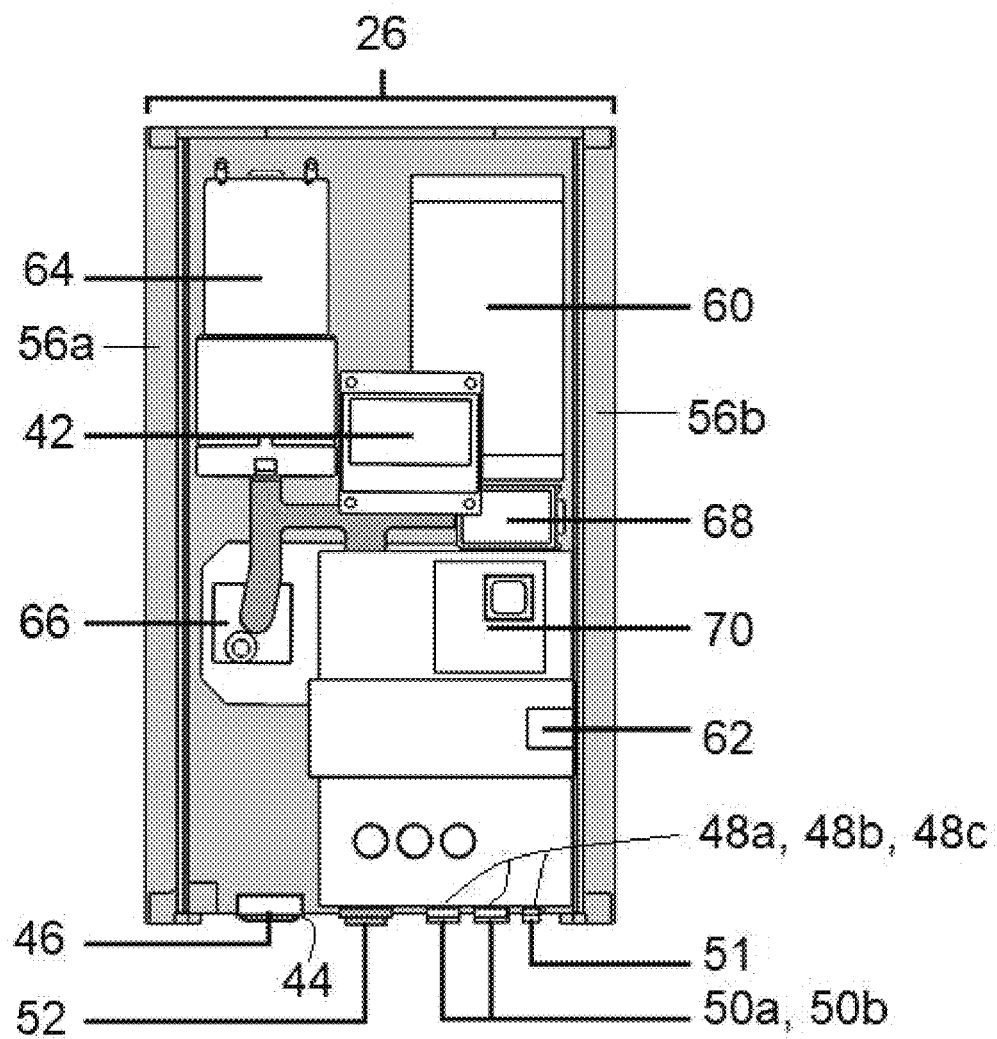
FIG. 5B is a perspective view of the cuff module of FIG. 5A, with the housing partially removed to show the internal components of the cuff module.

In the various embodiments shown in FIG. 5A, an exemplary cuff module (12a, 12b, 12c, 12d) for use with the system (1) generally comprises a housing (26) defining an inner cavity (28) for encasing all internal components as shown in FIG. 5B of the cuff module (12a, 12b, 12c, 12d). In the various embodiments, the housing (26) is configured to be tightly sealed, resistant to liquids, and easily sanitized or disinfected for medical use. The components of the system (1) are made with materials and surfaces that are easy to disinfect using chemicals or UV light, while also being resistant to degradation using such disinfection methods. In the various embodiments, the housing (26) may be shaped to correspond to the shape of the arm cuff (14a, 14b) or leg cuff (16a, 16b). In the various embodiments, the housing (26) may be substantially rectangular-shaped to correspond with the rectangular-shape of the arm cuff (14a, 14b) or leg cuff (16a, 16b).

In the various embodiments, the housing (26) includes a front portion (30), a back portion (32), side portions (34a, 34b), a top portion (36), and a bottom portion (38). In the various embodiments, the front portion (30) defines a window (40) configured for receiving and accommodating a module display (42) for indicating system information. In the various embodiments, the bottom portion (38) of the housing (26) defines an aperture (44) configured for receiving and accommodating a power switch (46) to turn the cuff module (12a, 12b, 12c, 12d) "ON/OFF" as required. In the various embodiments, the bottom portion (38) defines one or more apertures (48a, 48b, 48c) configured for receiving and accommodating one or more input/outputs (50a, 50b) for wired connection to sensors including, but not limited to, the ECG module (18) and the pulse oximeter (20), and a charging port (51) for charging the internal battery (60).

In the various embodiments, the bottom portion (38) defines a cuff air outlet (52) which receives an air line (54) which connects the cuff module (12a, 12b, 12c, 12d) to the arm cuff (14a, 14b) or leg cuff (16a, 16b) and allows the passage of air therethrough to inflate or deflate the arm cuff (14a, 14b) or leg cuff (16a, 16b) to which the cuff module (12a, 12b, 12c, 12d) is connected.

In the various embodiments, the top and bottom portions (36, 38) are attached to the housing (26) by suitable attachment means (58a, 58b, 58c, 58d) including, but not limited to, screws, pins, and the like. The top and bottom portions (36, 38) define aligned outwardly extending protrusions (37a, 37b, 37c, 37d) configured for receiving corresponding mounting members (56a, 56b). The mounting members (56a, 56b) comprise posts oriented parallel to each other and offset from the side portions (34a, 34b) to define slots (41a, 41b) therebetween (FIG. 7).

Figure 7:
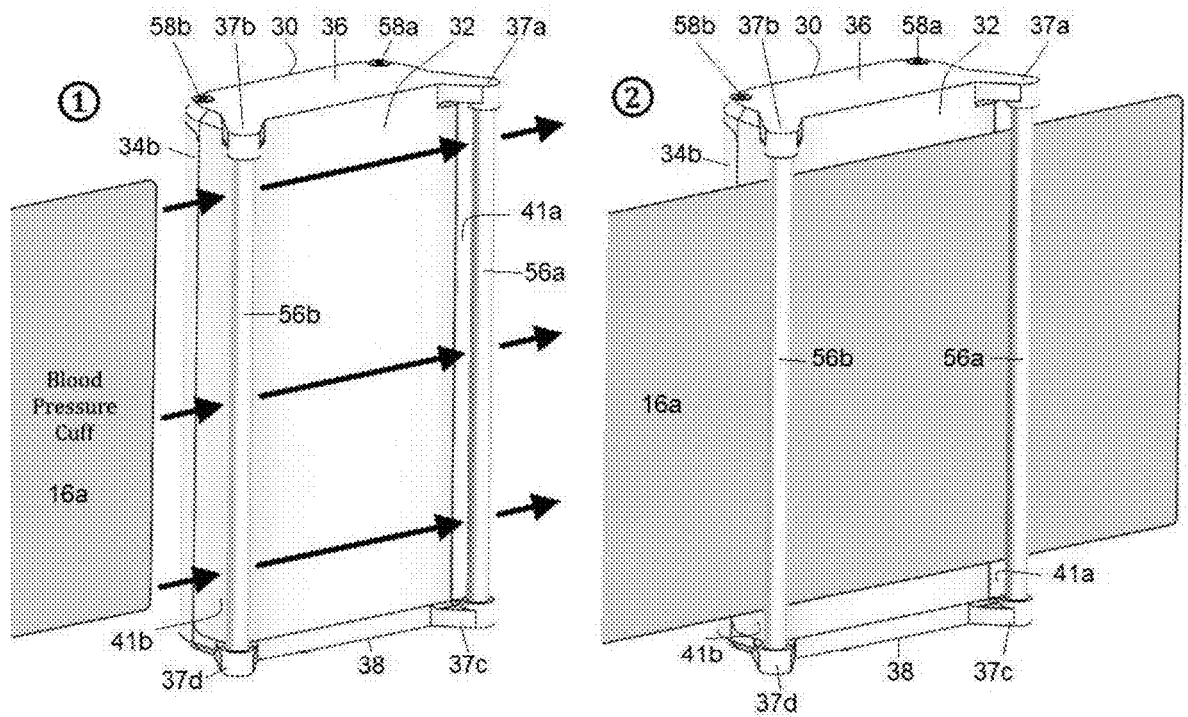
FIG. 7 is a perspective view showing mounting of the cuff module of FIG. 5A or 6 to a blood pressure cuff by threading the blood pressure cuff through slots provided at the back of the cuff module.

The mounting members (56a, 56b) attach the cuff module (12a, 12b, 12c, 12d) to various custom or off-the-shelf arm cuffs (14a, 14b) or leg cuffs (16a, 16b) which are threaded through the slots (41a, 41b) on the back portion (32) of the cuff module (12a, 12b, 12c, 12d) facing the patient's arm (arrows, FIG. 7). In the various embodiments, the arm cuffs (14a, 14b) and leg cuffs (16a, 16b) are blood pressure or other pneumatic cuffs. The cuff modules (12a, 12b, 12c, 12d), arm cuffs (14a, 14b), and leg cuffs (16a, 16b) are configured to be durable, secure, and easily attachable or removable.

In the various embodiments, custom blood pressure or pneumatic cuffs (14a, 14b, 16a, 16b) may be manufactured with an integrated holder for the cuff module (12a, 12b, 12c, 12d). This includes situations where the system is used for ECP therapy wherein additional cuffs may be deployed around the patient's calves, buttocks, hips and/or abdomen in addition to their thighs. In the various embodiments, attachment of the blood pressure or pneumatic cuff (14a, 14b, 18a, 18b) and system (1) to the patient would depend on the properties of the specific blood pressure or pneumatic cuff being deployed. With regard to most off-the-shelf blood pressure cuffs, the cuff (14a, 14b, 18a, 18b) wraps around the limb and is secured using a hook-and-loop fastener.

Figure 5C:
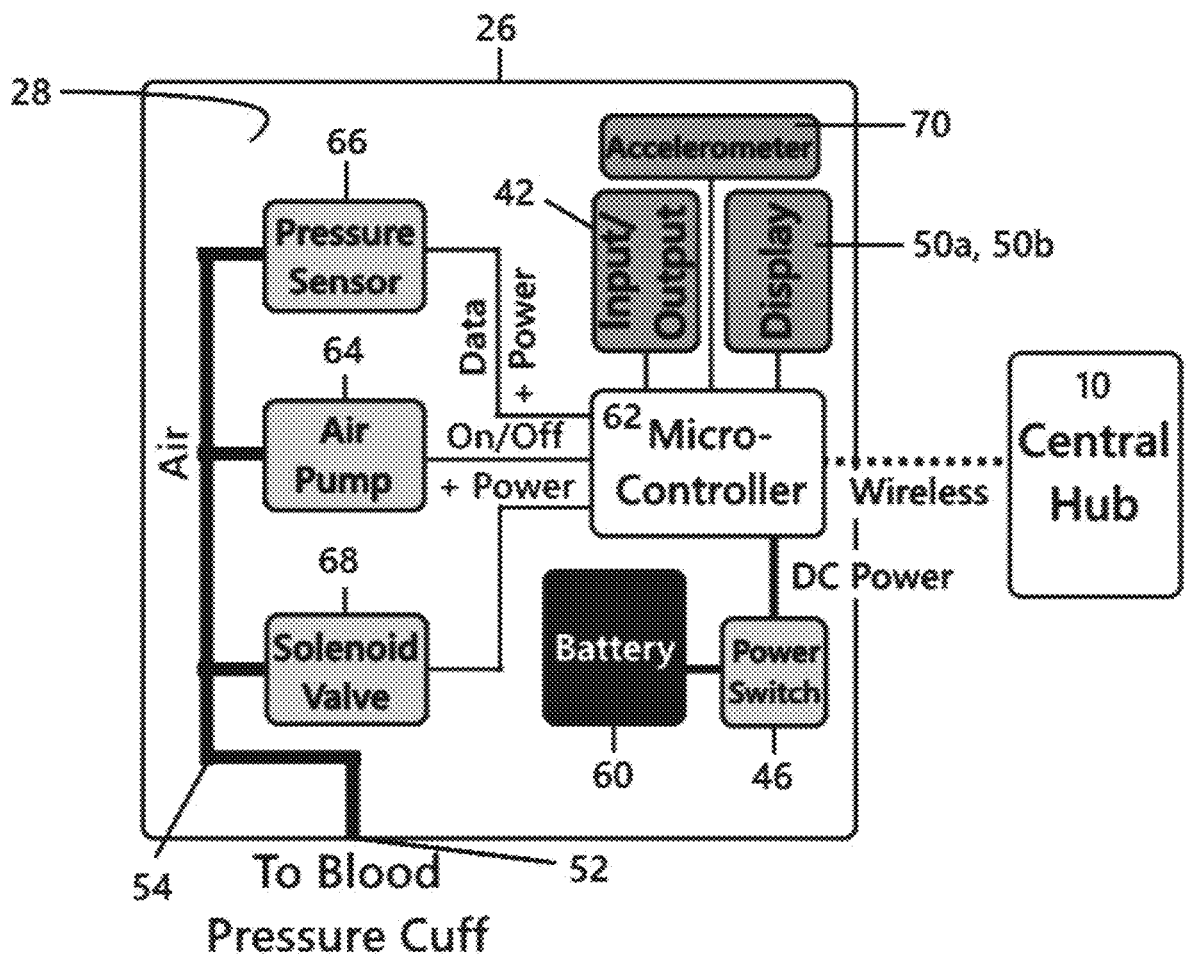
FIG. 5C is a block diagram showing connections among the internal components of the cuff module of FIG. 5A and wireless connection of the cuff module of FIG. 5A with the central hub.

FIG. 5B shows the housing (26) partially removed to show the internal components of the cuff module (12a, 12b, 12c, 12d). In the various embodiments, the internal components comprise one or more of an internal battery (60), a microcontroller (62), an air pump (64), a pressure sensor (66), a solenoid valve (68), and an accelerometer (70). In the various embodiments shown in FIG. 5C, the internal components, particularly through the microcontroller (62), intercommunicate with the central hub (10) to receive or transmit signals in order to perform selected functions. In the various embodiments, the internal components of the cuff module (12a, 12b, 12c, 12d) intercommunicate using wired communication, while the microcontroller (62) communicates with the central hub (10) using wireless communication.

In the various embodiments, the internal battery (60) provides direct current electricity to power the internal components, negating the need to connect the cuff module (12a, 12b, 12c, 12d) to an electricity supply. The battery (60) is connected to the power switch (46) such that in the "ON" position of the power switch (46), the battery (60) supplies power to the internal components, activating the cuff module (12a, 12b, 12c, 12d). Conversely, in the "OFF" position, the battery (60) ceases the power supply to the internal components, deactivating the cuff module (12a, 12b, 12c, 12d).

In the various embodiments, the microcontroller (62) comprises a wireless transceiver to receive commands from the central hub (10) and to transmit signals representing data received from the internal components to the central hub (10). In the various embodiments, the microcontroller (62) controls all functions of the cuff module (12a, 12b, 12c, 12d). The microcontroller (62) generates and transmits output signals to control the internal components, and also receives and is responsive to signals received from the internal components.

In the various embodiments, the air pump (64) and solenoid valve (68) cooperate to inflate and deflate the arm cuffs (14a, 14b) and leg cuffs (16a, 16b). In the various embodiments, the air pump (64) pressurizes the air line, arm cuffs (14a, 14b), and leg cuffs (16a, 16b). In the various embodiments, the pressure sensor (66) monitors the pressure. Depending on the treatment protocol being implemented, this enables the system (1) to adjust the target pressure of inflation or deflation based on the patient's monitored physiological pressure. In the various embodiments, the solenoid valve (68) releases air pressure as needed.

In the various embodiments, the accelerometer (70) filters out noise which may interfere with accurate reading of pressure (for example, while a subject is transported in an ambulance), and measure limb movement as a reflection of limb strength. In the various embodiments, the accelerometer (70) quantifies clinically relevant stroke progression. Currently, stroke progression is determined by paramedics in transport using very crude examination methods such as the assessment of the subject's ability to lift his/her arm, move fingers, squeeze his/her hand, or the presence of arm "drift." Such assessment is imprecise and qualitative. Even in the most unusual circumstance where there may be a stroke neurologist on the ambulance (such as in certain computed tomography scan-equipped mobile stroke units), the assessment at best relies on the National Institutes of Health Stroke Scale (NIHSS) score where limb strength can be graded across a few points, limiting the granularity of the information collected. Using accelerometers (70), ongoing feedback can be provided about the subject's clinical status especially in terms of how he/she is moving the limbs during inflation cycles (when there is resistance/pressure applied to the limb) or deflation cycles (when there is a natural instinct to move the limb to relieve tingling or other discomfort built up during the inflation cycle). The system (1) also facilitates side-to-side comparison of these data, which are especially relevant for stroke, as major stroke often presents as a reduction in strength (and therefore mobility) on one side of the body.

Figure 8:
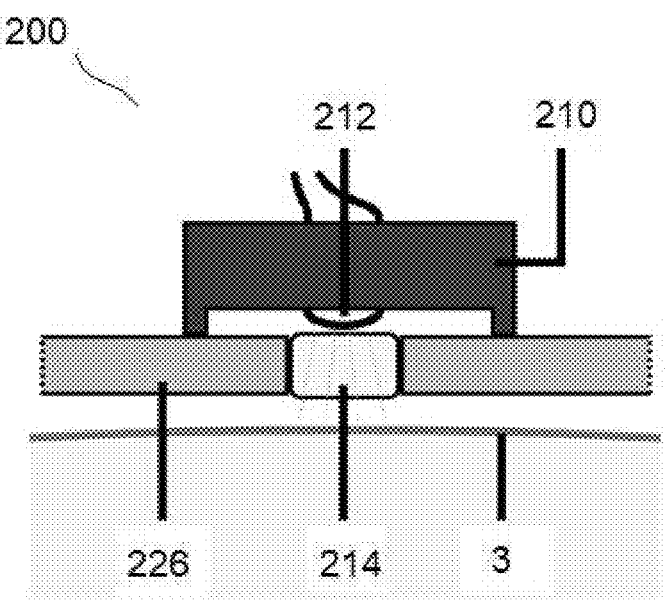
FIG. 8 is a schematic cross-sectional side view of a portion of a third embodiment of a cuff module for use with the system of FIG. 1 in position on the skin surface of the subject shown in FIG. 2.

In the various embodiments shown in FIG. 8, an exemplary cuff module (200) comprises a sensor (210) including a sensor transducer (212) disposed within the housing (226) of the cuff module (200). In the various embodiments, the sensor transducer (212) comprises a light-emitting diode ("LED"). The sensor (210) is capable of interacting with the skin surface (3) of the subject through provision of a clear shield (214) defined in the housing (226) through which the light from the sensor transducer (212) may be transmitted to the skin surface (3). While being encased within the cuff module (200), the internal sensor (210) is regardless capable of detecting a particular desired parameter external to the cuff module (200), thereby protecting both the subject's skin and the internal components of the cuff module (200). In the various embodiments, it will be appreciated that the clear shield (214) may be replaced with an electrode-based sensor (not shown) that would operate in a similar manner in contact with the subject's skin.

In the various embodiments, it will be appreciated that safety features have been incorporated within the system (1). The modular nature of the system (1) allows the components to be easily disconnected for thorough disinfecting protocols, followed by easy reassembly. Ongoing therapy can be immediately terminated not only through a central hub command but also manually through the power switch (46) on each cuff module (12a, 12b, 12c, 12d), in addition to the quick-release mechanism of the arm and leg cuffs (14a, 14b, 16a, 16b) which are replaceable or swappable with regular blood pressure cuffs. The cuff module (12a, 12b, 12c, 12d) can thus be easily turned off by an unsupervised patient (potentially even with some residual disability or weakness from a prior stroke) if using the system (1) at home for secondary prevention. Using its monitoring capabilities, each individual cuff module (12a, 12b, 12c, 12d) is also able to detect mission-critical scenarios when therapy may be unsafe or the patient is in a type of danger that takes priority over the treatment. In such settings, the system (1) either terminates or does not initiate the therapy cycle, sending an alert to the user at the central hub (10) and/or to the remote viewer. Visual signals are desirable where alarms may not be audible in a noisy environment or from a distance. However, audible alarms or output messages to hand-held devices, multiprocessor systems, microprocessor-based or programmable consumer electronics, personal computers, network PCs, mini-computers, mainframe computers, mobile phones, smart phones, tablets, personal digital assistants, and the like, may also be provided.

Figure 9A:
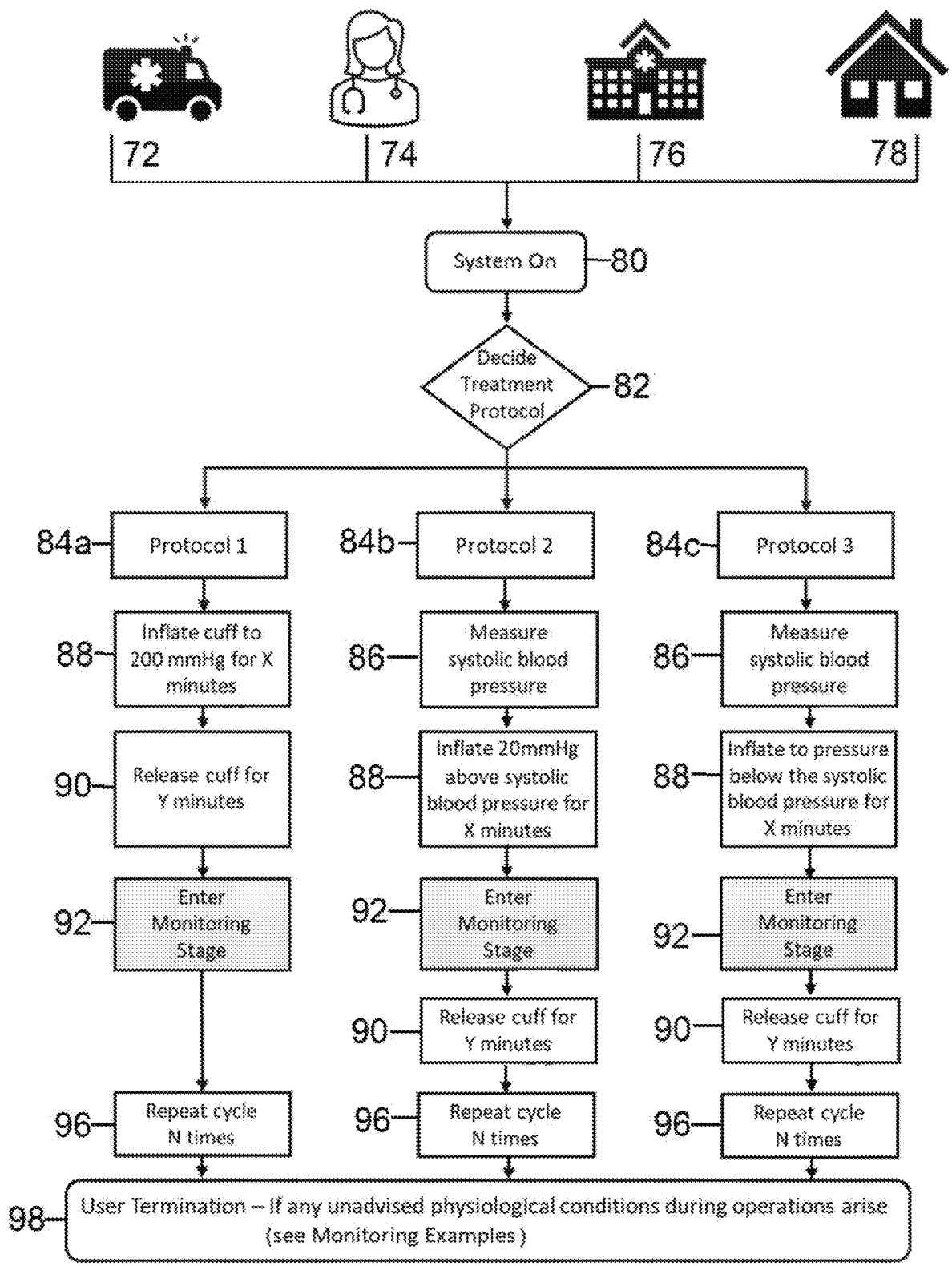
FIGS. 9A and 9B are flow diagrams showing exemplary treatment protocols and case scenarios in which the system of FIG. 1 may be used.
Figure 9B:
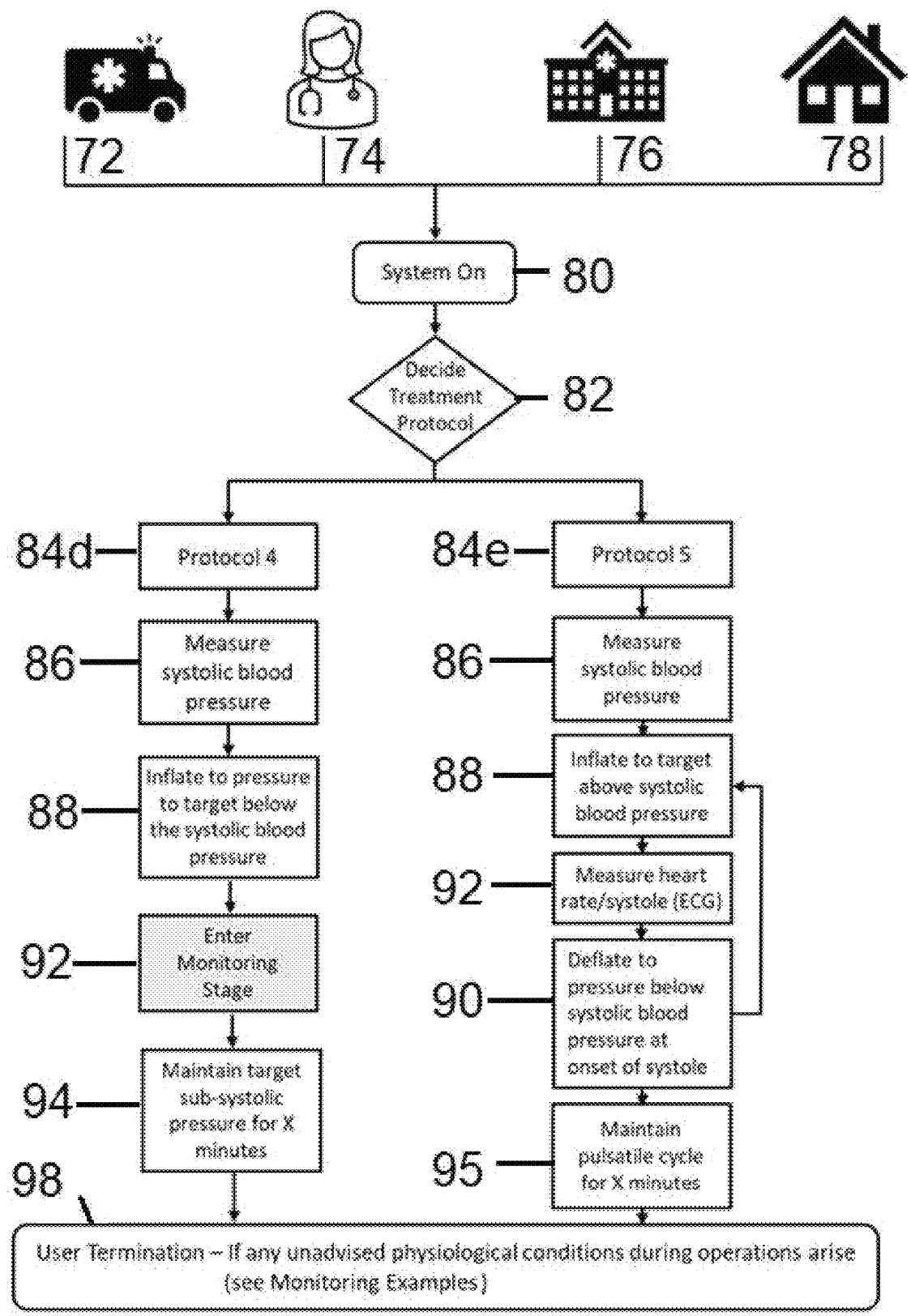

In the various embodiments shown in FIGS. 9A-B, the system (1) may be used in various exemplary treatment protocols and settings. As used herein, the term "setting" refers to a locale including, but not limited to, a transport vehicle such as, for example, an ambulance (72) for suspected strokes and myocardial infarctions; a hospital such as, for example, a surgical suite (74) to protect from embolic or other ischemic events, emergency department (76) while a patient is waiting for definitive therapy for stroke or myocardial infarction, scanner, or angiography suite; and the subject's home or an outpatient clinic (78) to prevent cardiovascular events, vascular cognitive impairment, etc. In the various embodiments, the system (1) may be used by the subject at home or in an outpatient setting with supervision or unsupervised as a prescribed therapy to prevent future ischemic events. For all possible settings, it will be appreciated that the system (1) is wireless, compact, user-friendly, and inexpensive.

Exemplary case scenarios for use of the system (1) may include, but are not limited to, (a) treatment of a patient with acute ischemic stroke during transit to a primary stroke center in an ambulance, or while waiting in the emergency department, scanner, or angiography suite, with the intention of preserving as much brain tissue as possible before definitive reperfusion therapies like thrombolysis or thrombectomy can be administered; (b) treatment of a patient with an acute coronary syndrome during transit to hospital, or while waiting in the emergency department or angiography suite, with the intention of preserving as much myocardial tissue as possible before definitive reperfusion therapies like thrombolysis or percutaneous coronary interventions can be administered; (c) neuro-protection or cardio-protection during surgical or radio-interventional procedures where there is a risk of ischemic damage, such as carotid endarterectomy/stenting, repair of aneurysms or other vascular malformations, aortic surgeries, or any cardiac procedure (coronary artery bypass, valvular surgery, etc.); and (d) home- or clinic-based long-term treatment (with regimens like RIC or ECP) with the intention of preventing the progression of heart disease, cerebral small vessel disease, or vascular cognitive impairment, or the recurrence of emergencies like acute coronary syndrome or stroke.

Depending on the case scenario for use of the system, the system hardware can be suitably adapted. For example, in a setting that requires only one cuff module and no central hub (10), the cuff module (12a, 12b, 12c, 12d) may be configured as a standalone device with a single charging dock and with additional control buttons (71) (FIG. 6). The internal hardware, such as the air pump (64), internal battery (60), pressure sensor (66), solenoid valve (68), or other electronics may also differ between different settings, depending on the needs. For example, the internal battery (60) may be made larger for use in cases that require extended use between charges. The air pump (64) may also be sized differently depending on the rate or pressure of inflation required. The housing (26) may also differ depending on the setting. An ambulance, hospital or operating room housing (26) may be designed with better durability than for example, a home housing (26). In another configuration, the mounting members (56a, 56b) for an ambulance setting may be designed to take up less space, be faster with docking/undocking, and have stronger latches, whereas home mounting members (56a, 56b) may be designed for ease-of-use and simplicity of manufacturing.

In use as shown in FIGS. 9A-B, at step (80), the desired number of arm cuffs (14a, 14b) and leg cuffs (16a, 16b) and corresponding attached cuff modules (12a, 12b, 12c, 12d) are positioned on the subject's arms and legs. In the various embodiments, a maximal four-limb dose is applied. Additional sensors (18, 20) may be positioned on parts of the subject's body other than the arms and legs. The system (1) is activated by placing the power switch (46) of each cuff module (12a, 12b, 12c, 12d) to the "ON" position. Based on the patient's disease condition, step (82) involves selecting a suitable treatment protocol from among multiple protocols (84a, 84b, 84c, 84d, 84e). In this manner, the clinician may control the duration and dose of RIC in a coordinated manner. Steps within the selected protocol may include, but are not limited to, measurement of systolic blood pressure (86), inflation (88) or deflation (90) of the cuff (14a, 14b, 16a, 16b) for a predetermined time period, entering a monitoring stage (92), maintaining a target sub-systolic pressure (94), maintaining a pulsatile cycle for a predetermined time period (95), and repeating the cycle a predetermined number of times (96). Without being bound by any theory, cycling between occlusion of blood flow and reperfusion for specified time intervals may induce RIC.

In the various embodiments, each cuff module (12a, 12b, 12c, 12d) may also run a different protocol or run the same protocol at different times, as each cuff (14a, 14b, 16a, 16b) is able to deliver the therapy to the arm or leg independent of the rest. In the various embodiments, the system (1) can be programmed to automatically have one turned off and have the other three going in a rotating pattern (or 2-off/2-on or 3-off/1-on) to tailor the protocol for patient tolerability.

In the various embodiments, the system (1) can be programmed to administer traditional RIC protocols of occlusion (inflation to 20 mmHg above the systolic pressure or 200 mmHg) and reperfusion (deflation) or inflation to a sub-systolic pre-specified pressure. To permit testing of the latter protocol, the system (1) can also be programmed to inflate the cuffs (14a, 14b, 16a, 16b) to a pre-set sub-occlusive pressure and remain at that level of inflation for the duration of therapy.

In the various embodiments, the system (1) can also be programmed to deliver ECP therapy. The system (1) as described here will be able to deliver automated ECP therapy through multiple lower limb-attached devices. Based on parameters set by the user, the system (1) will rapidly inflate during diastole and deflate during systole to increase diastolic blood pressure. The wireless compact design encourages use in not only acute ambulance, operation theatre, or hospital settings, but also in home- or outpatient clinic-based settings where both device size and ease-of-use have previously limited the use of ECP therapy. Furthermore, as the duration of therapy and optimal pressures to achieve are currently unknown, the system (1) described can be programmed to achieve select pressures and durations to allow for the testing of various protocols in a research setting (FIGS. 9A-B). When administering an ECP-like protocol, larger cuffs may be deployed around the patient's hips, buttocks, and/or abdomen, synchronized with the limb protocols.

Figure 10:
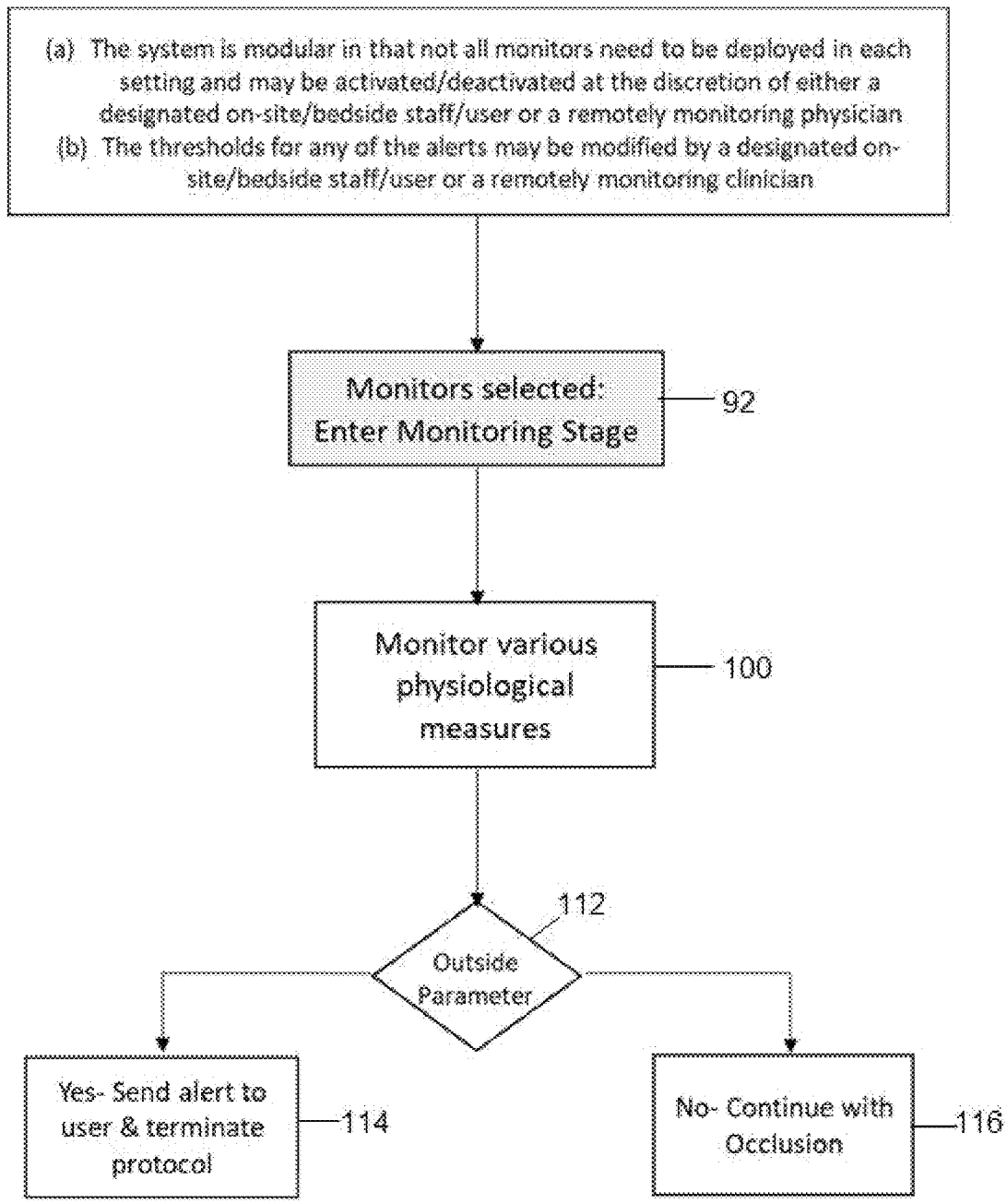
FIG. 10 is a flow diagram showing exemplary monitoring protocols in which the system of FIG. 1 may be used.
Figure 11A:
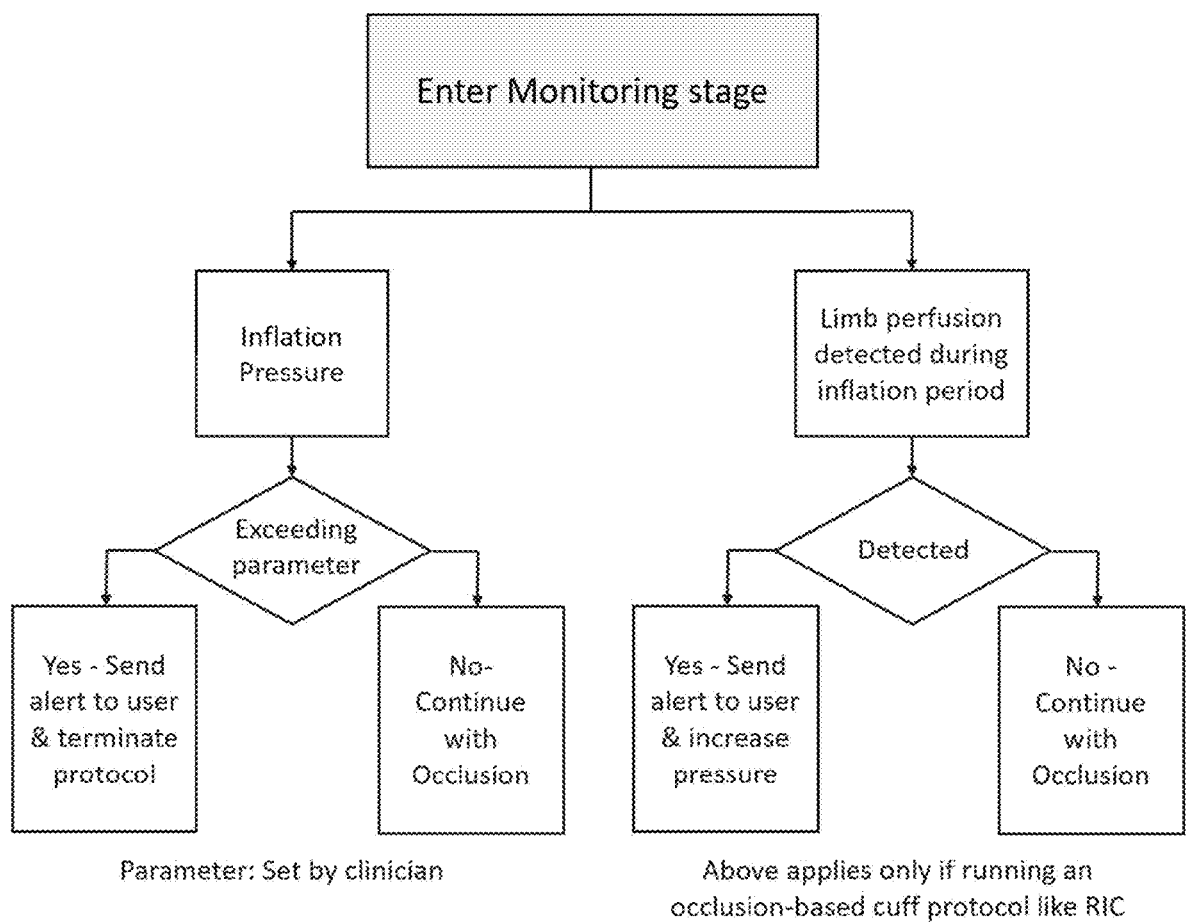
FIGS. 11A, 11B, 11C, and 11D are flow diagrams showing exemplary parameters which may be monitored using the system of FIG. 1 in order to adjust treatment protocols as required.
Figure 11B:
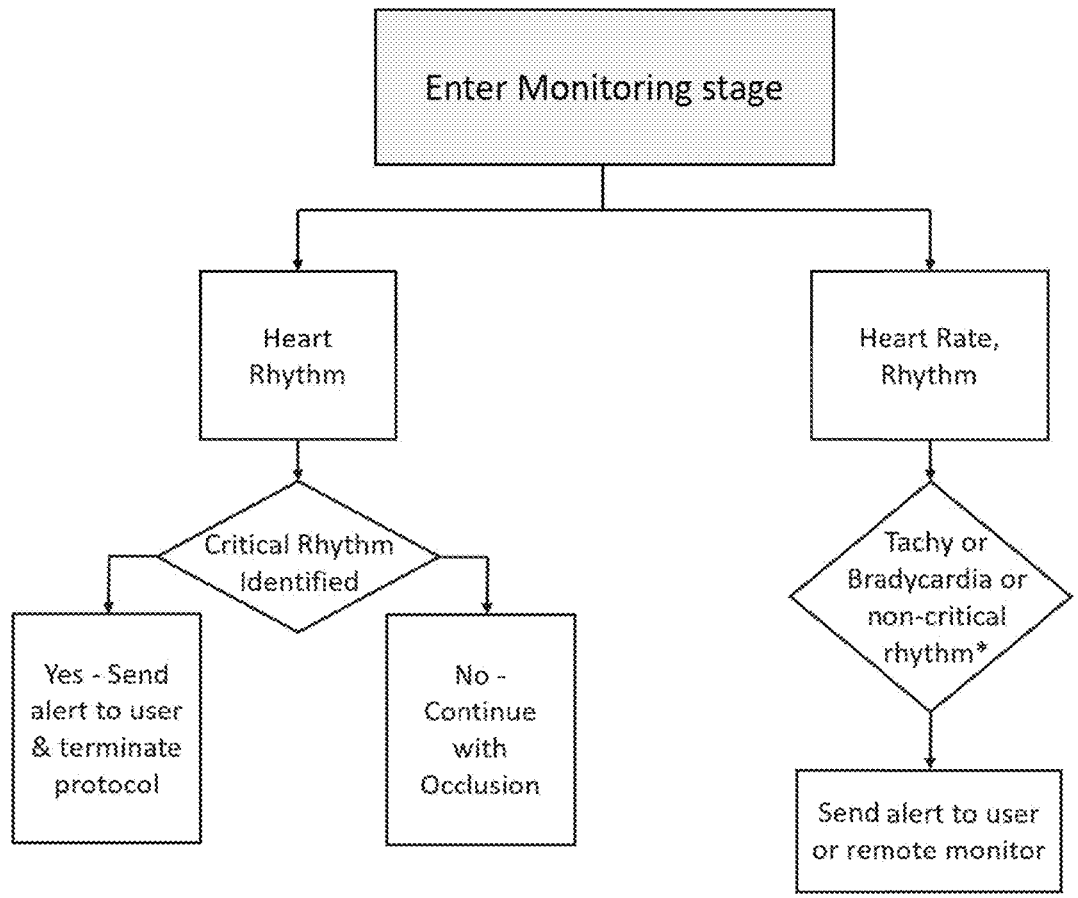
Figure 11C:
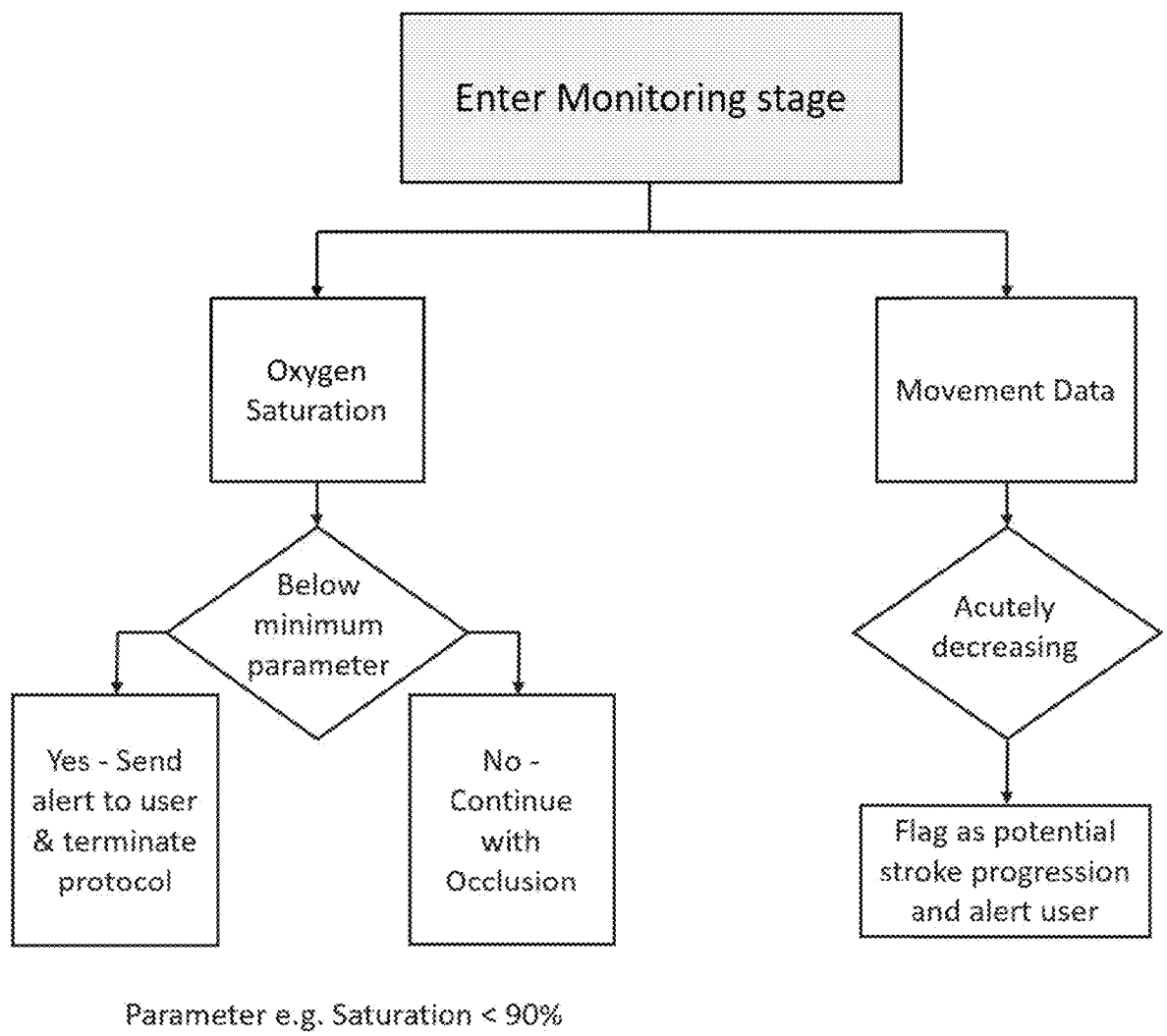
Figure 11D:
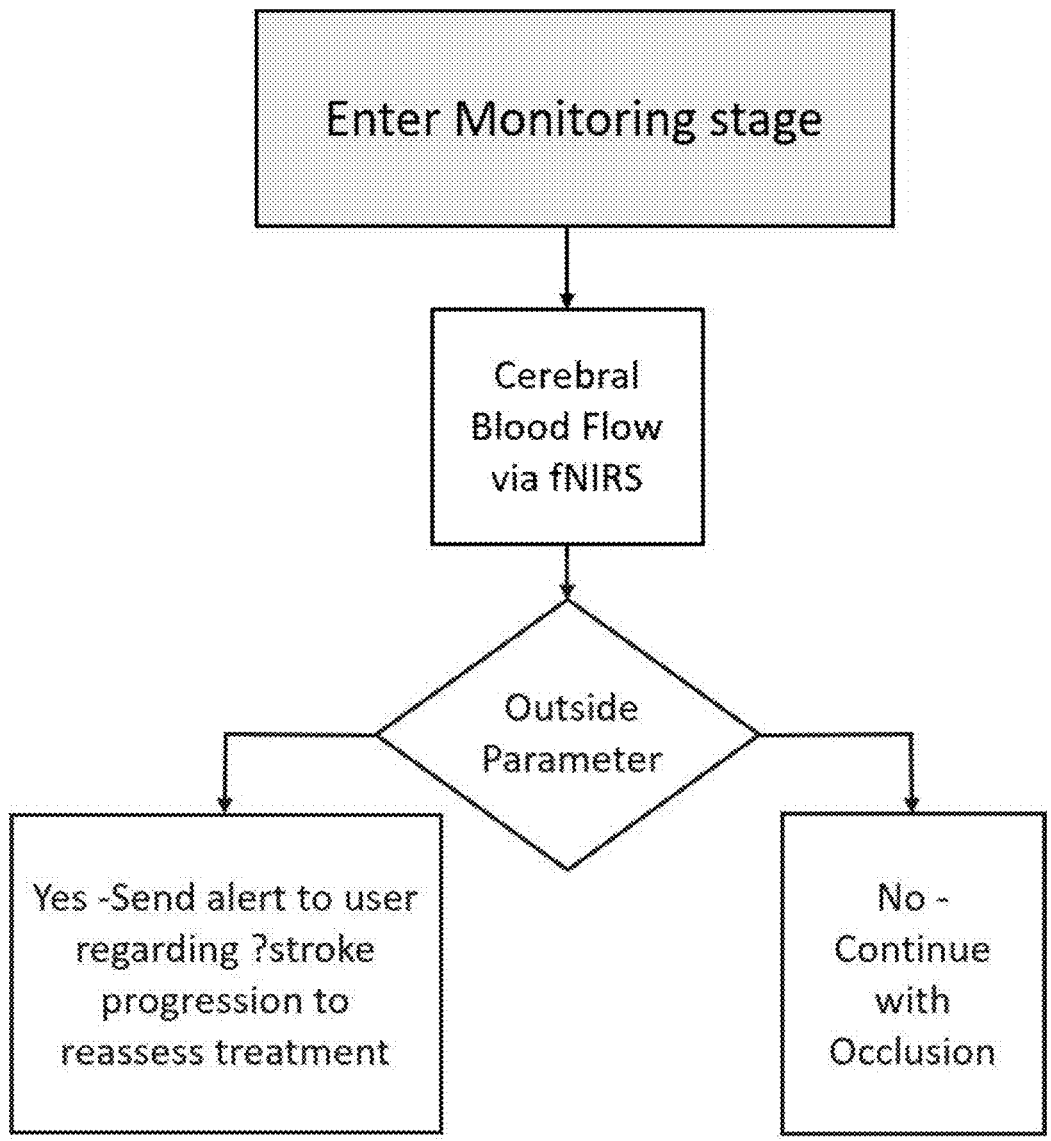

In step (98), the therapy may be terminated upon completion or before completion in the event that unadvised physiological conditions for operation arise. As shown in FIGS. 9A-B, all protocols enter a monitoring stage to ensure the safety of the patient during therapy. As shown in FIG. 10, at steps (92, 100), various physiological measures may be selected and monitored. If a measure falls outside a predetermined threshold at step (112), an alert is sent to the user to terminate the therapy (step 114); otherwise, therapy continues safely (step 116). FIGS. 11A-D show key examples of parameters that can be monitored by the system (1) and the alerts or amendments that can be made to the protocols in response to safety concerns raised through the monitors. Such parameters may include, but are not limited to, inflation pressure, limb perfusion during inflation, heart rhythm, heart rate, oxygen saturation, movement data, cerebral blood flow, and the like.

As one example, the system (1) can provide details about peripheral limb ischemia through a pulse oximeter, issue a warning to personnel, and not apply therapy in such a case. An example of such a mission-critical situation might be if there is an unrecognized release of emboli during a cardiovascular surgical procedure that causes a vessel occlusion in the arms or legs.

As another example, in a case of extreme hypertension, the system (1) can provide warning/feedback about blood pressure to prevent cuff occlusion at a level that might theoretically result in a crush injury to blood vessels.

As yet another example, when communicating with heart rhythm monitors, the system (1) has the ability to continuously identify aberrant heart rhythms and issue warnings when clinically relevant rhythms like atrial fibrillation or atrial flutter are detected (alert issued but treatment continues). If emergent rhythms like ventricular tachycardia or ventricular fibrillation are detected, which require other critical treatments to be administered (such as defibrillation), the treatment will auto-terminate in addition to issuing an alert.

It should be apparent, however, to those skilled in the art that many more modifications besides those already described are possible without departing from the inventive concepts herein. The inventive subject matter, therefore, is not to be restricted except in the scope of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

All publications mentioned are incorporated herein by reference (where permitted) to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.
1. Stokfisz K, Ledakowicz-Polak A, Zagorski M, Zielinska M. Ischaemic preconditioning-Current knowledge and potential future applications after 30 years of experience. Advances in medical sciences 2017; 62:307-316.
2. Pan J, Li X, Peng Y. Remote ischemic conditioning for acute ischemic stroke: dawn in the darkness. Reviews in the neurosciences 2016; 27:501-510.
3. Berger M M, Macholz F, Mairbaurl H, Bartsch P. Remote ischemic preconditioning for prevention of high-altitude diseases: fact or fiction? Journal of applied physiology 2015; 119:1143-1151.
4. Hess D C, Blauenfeldt R A, Andersen G, et al. Remote ischaemic conditioning-a new paradigm of self-protection in the brain. Nature reviews Neurology 2015; 11:698-710.
5. Rassaf T, Totzeck M, Hendgen-Cotta U B, Shiva S, Heusch G, Kelm M. Circulating nitrite contributes to cardioprotection by remote ischemic preconditioning. Circulation research 2014; 114:1601-1610.
6. Li J, Rohailla S, Gelber N, et al. MicroRNA-144 is a circulating effector of remote ischemic preconditioning. Basic research in cardiology 2014; 109:423.
7. Cai Z P, Parajuli N, Zheng X, Becker L. Remote ischemic preconditioning confers late protection against myocardial ischemia-reperfusion injury in mice by upregulating interleukin-10. Basic research in cardiology 2012; 107: 277.
8. Hougaard K D, Hjort N, Zeidler D, et al. Remote ischemic perconditioning as an adjunct therapy to thrombolysis in patients with acute ischemic stroke: a randomized trial. Stroke 2014; 45:159-167.
9. McLeod S L, Iansavichene A, Cheskes S. Remote ischemic preconditioning to reduce reperfusion injury during acute S T-segment-elevation myocardial infarction: A systematic review and meta-analysis. J Am Heart Assoc 2017; 6.
10. Blusztein D I, Brooks M J, Andrews D T. A systematic review and meta-analysis evaluating ischemic conditioning during percutaneous coronary intervention. Future Cardiol 2017; 13:579-592.
11. Pierce B, Bole I, Patel V, Brown D L. Clinical outcomes of remote ischemic preconditioning prior to cardiac surgery: A meta-analysis of randomized controlled trials. J Am Heart Assoc 2017; 6.
12. Meng R, Ding Y, Asmaro K, et al. Ischemic Conditioning Is Safe and Effective for Octo- and Nonagenarians in Stroke Prevention and Treatment. Neurotherapeutics: the journal of the American Society for Experimental NeuroTherapeutics 2015; 12:667-677.
13. Meng R, Asmaro K, Meng L, et al. Upper limb ischemic preconditioning prevents recurrent stroke in intracranial arterial stenosis. Neurology 2012; 79:1853-1861.
14. Mi T, Yu F, Ji X, Sun Y, Qu D. The Interventional Effect of Remote Ischemic Preconditioning on Cerebral Small Vessel Disease: A Pilot Randomized Clinical Trial. European neurology 2016; 76:28-34.
15. Wang Y, Meng R, Song H, et al. Remote Ischemic Conditioning May Improve Outcomes of Patients With Cerebral Small-Vessel Disease. Stroke 2017; 48:3064-3072.
16. Bilgin-Freiert A, Dusick J R, Stein N R, Etchepare M, Vespa P, Gonzalez N R. Muscle microdialysis to confirm sublethal ischemia in the induction of remote ischemic preconditioning. Translational stroke research 2012; 3:266-272.
17. Zhao W, Meng R, Ma C, et al. Safety and Efficacy of Remote Ischemic Preconditioning in Patients With Severe Carotid Artery Stenosis Before Carotid Artery Stenting: A Proof-of-Concept, Randomized Controlled Trial. Circulation 2017; 135:1325-1335.
18. England T J, Hedstrom A, O'Sullivan S, et al. RECAST (Remote Ischemic Conditioning After Stroke Trial): A Pilot Randomized Placebo Controlled Phase II Trial in Acute Ischemic Stroke. Stroke 2017; 48:1412-1415.
19. Koch S, Katsnelson M, Dong C, Perez-Pinzon M. Remote ischemic limb preconditioning after subarachnoid hemorrhage: a phase Ib study of safety and feasibility. Stroke 2011; 42:1387-1391.
20. Schellinger P D, Shuaib A, Kohrmann M, et al. Reduced mortality and severe disability rates in the SENTIS trial. AJNR Am J Neuroradiol 2013; 34:2312-2316.
21. Shuaib A, Bornstein N M, Diener H C, et al. Partial aortic occlusion for cerebral perfusion augmentation: safety and efficacy of NeuroFlo in Acute Ischemic Stroke trial. Stroke 2011; 42:1680-1690.
22. Raza A, Steinberg K, Tartaglia J, Frishman W H, Gupta T. Enhanced External Counterpulsation Therapy: Past, Present, and Future. Cardiol Rev 2017; 25:59-67.
23. Soran O, Kennard E D, Kfoury A G, Kelsey S F, Investigators I. Two-year clinical outcomes after enhanced external counterpulsation (EECP) therapy in patients with refractory angina pectoris and left ventricular dysfunction (report from The International EECP Patient Registry). Am J Cardiol 2006; 97:17-20.
24. Guluma K Z, Liebeskind D S, Raman R, et al. Feasibility and Safety of Using External Counterpulsation to Augment Cerebral Blood Flow in Acute Ischemic Stroke—The Counterpulsation to Upgrade Forward Flow in Stroke (CUFFS) Trial. J Stroke Cerebrovasc Dis 2015; 24:2596-2604.
25. Han J H, Leung T W, Lam W W, et al. Preliminary findings of external counterpulsation for ischemic stroke patient with large artery occlusive disease. Stroke 2008; 39:1340-1343.
26. Lin S, Liu M, Wu B, Hao Z, Yang J, Tao W. External counterpulsation for acute ischaemic stroke. Cochrane Database Syst Rev 2012; 1: CD009264.
27. ScottCare ViaCare™ ECP [online]. Available at: http://camelin.tech/en/viacare-ecp/. Accessed May 6.
28. Luminair™ EECP® Therapy System [online]. Available at: https://www.vasomeditech.com/luminair.html/. Accessed May 6.
29. Pureflow [online]. Available at: http://xtreempulse.com/pureflow.html. Accessed May 6.

What is claimed is:

1. A system for preventing, treating, or alleviating ischemic and non-ischemic disease in a subject comprising:
   wearable limb cuffs positionable about multiple limbs and configured to inflate or deflate about the multiple limbs,
   a central hub, and
   cuff modules in wireless communication with the central hub, the cuff modules being connectable and mountable to the corresponding wearable limb cuffs,
   wherein the central hub is configured to charge the cuff modules and to transmit commands wirelessly to the cuff modules to inflate or deflate the wearable limb cuffs about the multiple limbs for coordinated delivery of same or different multiple therapies according to treatment protocols or sham protocols, each of the cuff modules being capable of delivering therapies independently of other cuff modules and activated in rotating patterns; and to receive, collect, and store data from the cuff modules and one or more sensors on one or more cloud-based servers for display in-near-real time on one or more dashboard user interfaces configured to allow downloading of the data using the central hub to monitor one or more parameters representative of the subject's physiological condition and re-program the treatment protocols or sham protocols; and wherein the central hub comprises a smartphone, tablet, or computer comprising a processor and a non-transitory computer-readable medium including instructions that are executable by the processor to cause the processor to perform operations comprising:

based on the received, collected, and stored data, continuing, adjusting, or terminating the treatment protocols or the sham protocols remotely in near-real-time in accordance with the subject's monitored physiological condition, the treatment protocols or the sham protocols being programmable through the central hub remotely and comprising one or more treatment cycles of inflation or deflation of the limb cuffs to desired pressures for a set time and a monitoring stage, wherein the central hub provides auditory or visual feedback indicating progress of the one or more treatment cycles or system status, and wherein if a physiological measure of the subject falls outside a predetermined threshold, an alert is emitted to terminate treatment, or if the physiological measure of the subject falls within the predetermined threshold, the treatment continues;

wherein the physiological measure of the subject comprises a first set of parameters and/or a second set of parameters.

2. The system of claim 1, wherein each of the cuff modules is configured to monitor the first set of parameters selected from systolic and diastolic blood pressure, heart rate, oxygen saturation, accelerometry, and blood volume.

3. The system of claim 2, further comprising the one or more sensors to be attached to the subject's body parts other than limbs for monitoring the, second set of parameters.

4. The system of claim 3, wherein the one or more sensors are selected from an electrocardiogram module, a pulse oximeter, a near infrared spectroscopy, an electroencephalography module, a light-emitting diode, an electrode-based sensor, or a perfusion sensor.

5. The system of claim 4, wherein the one or more sensors are communicatively coupled to the central hub through wireless connection or through wired connection with the cuff modules.

6. The system of claim 1, wherein the wearable limb cuffs comprise blood pressure cuffs.

7. The system of claim 6, further comprising additional wearable cuffs to be worn around one or more of the subject's hips, buttocks, and abdomen.

8. The system of claim 3, wherein each of the cuff modules comprises a housing having a front portion, a back portion, side portions, a top portion, a bottom portion, and defining an inner cavity.

9. The system of claim 8, wherein the bottom portion defines an aperture configured for receiving and accommodating a power switch to activate or deactivate each of the cuff modules, one or more input/outputs for connecting the one or more sensors, and a charging port.

10. The system of claim 9, wherein the bottom portion defines a cuff air outlet for receiving an air line, the air line configured for connecting each of the cuff modules to the wearable limb cuff and allowing passage of air therethrough to inflate or deflate the corresponding wearable limb cuff.

11. The system of claim 8, further comprising mounting members for attaching each of the cuff modules to the corresponding wearable limb cuff.

12. The system of claim 11, wherein the top and bottom portions define outwardly aligned extending protrusions configured for receiving the mounting members, the mounting members comprising posts oriented parallel to each other and offset from the side portions to define slots therebetween for threading the corresponding wearable limb cuff.

13. The system of claim 8, wherein each of the cuff modules further comprises one or more of a battery, a microcontroller, an air pump, a pressure sensor, a solenoid valve, an accelerometer, a speaker, a buzzer, and an additional control button for enabling delivery of therapy during unavailability or failure of the central hub or wireless communication.

14. The system of claim 13, wherein the microcontroller comprises a wireless transceiver for receiving commands from the central hub and for transmitting signals representing data received from the cuff modules and the one or more sensors to the central hub.

15. The system of claim 14, wherein the air pump and the solenoid valve cooperate to inflate and deflate the wearable limb cuffs.

16. A method for preventing, treating, or alleviating ischemic and non-ischemic disease in a subject comprising:

providing a system comprising wearable limb cuffs positionable about multiple limbs and configured to inflate or deflate about the multiple limbs, a central hub comprising a smartphone, tablet, or computer, and cuff modules in wireless communication with the central hub, the cuff modules being connectable and mountable to the corresponding wearable limb cuffs;

positioning the wearable limb cuffs and the corresponding cuff modules on the multiple limbs of the subject; and activating the system, wherein the central hub charges the cuff modules and transmits commands wirelessly to the cuff modules to inflate or deflate the wearable limb cuffs about the multiple limbs for coordinated delivery of same or different multiple therapies, each of the cuff modules being capable of delivering therapies independently of other cuff modules and activated in rotating patterns, according to treatment protocols or sham protocols including one or more treatment cycles comprising inflation or deflation of the limb cuffs to desired pressures for a set time and a monitoring stage before continuing, adjusting, or terminating the treatment protocols or the sham protocols, the treatment protocols or the sham protocols being programmable through the central hub remotely, and wherein the central hub receives, collects, and stores data from the cuff modules and one or more sensors on one or more cloud-based servers for display in near-real-time on one or more dashboard user interfaces configured to allow downloading of the data using the smartphone, tablet, or personal computer to monitor one or more parameters representative of the subject's physiological condition and re-program the treatment protocols or sham protocols; and based on the received, collected, and stored data, continuing, adjusting, or terminating the treatment protocols or the sham protocols remotely in near-real-time in accordance with the subject's monitored physiological condition, wherein the central hub provides auditory or visual feedback indicating progress of the one or more treatment cycles or system status, and wherein if a physiological measure of the subject falls outside a predetermined threshold, an alert is emitted to terminate treatment, or if the physiological measure of the subject falls within the predetermined threshold, the treatment continues.

17. The method of claim 16, further comprising positioning additional cuffs around the subject's hips, buttocks, or abdomen.

18. The method of claim 17, further comprising positioning sensors on the subject's body.

19. The method of claim 18, wherein the treatment protocols or the sham protocols comprise remote ischemic conditioning therapy with different thresholds or durations of inflation and deflation, external counterpulsation therapy, or sustained inflation to sub-systolic pressures.

20. The system of claim 1, wherein the central hub is configured to be operable on-site, in an ambulance, or at a remote site.

21. The method of claim 16, wherein the central hub is operable on-site, in an ambulance, or at a remote site.

22. The method of claim 19, wherein the treatment protocols or the sham protocols are delivered by the cuff modules during unavailability or failure of the central hub or wireless communication.

* * * * *